United States Patent
Zeiger et al.

(10) Patent No.: US 10,847,267 B1
(45) Date of Patent: *Nov. 24, 2020

(54) COMPUTER-BASED METHOD AND SYSTEM FOR FACILITATING VOICE CONSULTATIONS

(71) Applicant: CurbsideMDLive, Inc., Danville, CA (US)

(72) Inventors: Howard Zeiger, Danville, CA (US); Mike Ricci, Alamo, CA (US); Chris Hughes, Palo Alto, CA (US)

(73) Assignee: CURBSIDEMDLIVE, INC., Danville, CA (US)

( * ) Notice: Subject to any disclaimer, the term of this patent is extended or adjusted under 35 U.S.C. 154(b) by 143 days.

This patent is subject to a terminal disclaimer.

(21) Appl. No.: 15/960,386

(22) Filed: Apr. 23, 2018

Related U.S. Application Data

(63) Continuation-in-part of application No. 13/922,394, filed on Jun. 20, 2013, now Pat. No. 9,965,590.

(Continued)

(51) Int. Cl.
*G16H 80/00* (2018.01)
*G06Q 10/06* (2012.01)
(Continued)

(52) U.S. Cl.
CPC ....... *G16H 80/00* (2018.01); *G06Q 10/06311* (2013.01); *G06Q 10/1095* (2013.01); *H04M 3/436* (2013.01)

(58) Field of Classification Search
CPC .............. G06Q 10/109; G06Q 10/107; G06Q 30/0214; G06Q 30/0282; G06Q 10/06311; G06Q 50/22; H04M 3/436; G16H 80/00

(Continued)

(56) References Cited

U.S. PATENT DOCUMENTS 6,272,470 B1   8/2001   Teshima
2006/0026051 A1*   2/2006   Rose ................... G06Q 10/10
                                                               705/80

(Continued)

OTHER PUBLICATIONS

Zeiger, U.S. Appl. No. 15/483,857, filed Apr. 10, 2017, Office Action, dated Apr. 18, 2019.

(Continued)

*Primary Examiner* — Hiep V Nguyen
(74) *Attorney, Agent, or Firm* — Hickman Palermo Becker Bingham LLP; Christine E. Orich

(57) ABSTRACT

According to various embodiments, a collaboration system and methods are provided to enable consultants to efficiently collaborate with one another by engaging in system-facilitated voice consultations. As used herein, a voice consultation may generally refer to communications established between two or more users of the collaboration system. In general, the system and methods described herein provide the ability for users to establish voice consultations with other users at a mutually convenient time, whether or not there exists a prior relationship between the users. The system and methods automatically place a consultation call at a time requested by the caller and which the callee has previously announced as available. Called parties may determine whether to accept a consultation based on data that is visually perceptible with a mobile device at which the call is received.

12 Claims, 21 Drawing Sheets

Related U.S. Application Data

(60) Provisional application No. 61/661,904, filed on Jun. 20, 2012, provisional application No. 61/754,817, filed on Jan. 21, 2013.

(51) Int. Cl.
*G06Q 10/10* (2012.01)
*H04M 3/436* (2006.01)

(58) Field of Classification Search
USPC .......................................................... 705/2
See application file for complete search history.

(56) References Cited

U.S. PATENT DOCUMENTS

| | | |
|---|---|---|
| 2006/0045029 A1 | 3/2006 | Ethier |
| 2007/0038474 A1 | 2/2007 | Halsted |
| 2007/0291923 A1* | 12/2007 | Hsieh .................... H04M 7/003 379/265.01 |
| 2008/0021760 A1 | 1/2008 | Doss |
| 2010/0153487 A1 | 6/2010 | Greven |
| 2010/0293487 A1 | 11/2010 | Schoenberg |
| 2013/0103423 A1 | 4/2013 | Kim |
| 2013/0297324 A1 | 11/2013 | Phillips |

OTHER PUBLICATIONS

Zeiger, U.S. Appl. No. 15/783,857, filed Apr. 10, 2017, Advisory Action, dated Feb. 7, 2020.
Zeiger, U.S. Appl. No. 15/483,857, filed Apr. 10, 2017, Final Office Action, dated Nov. 26, 2019.

* cited by examiner

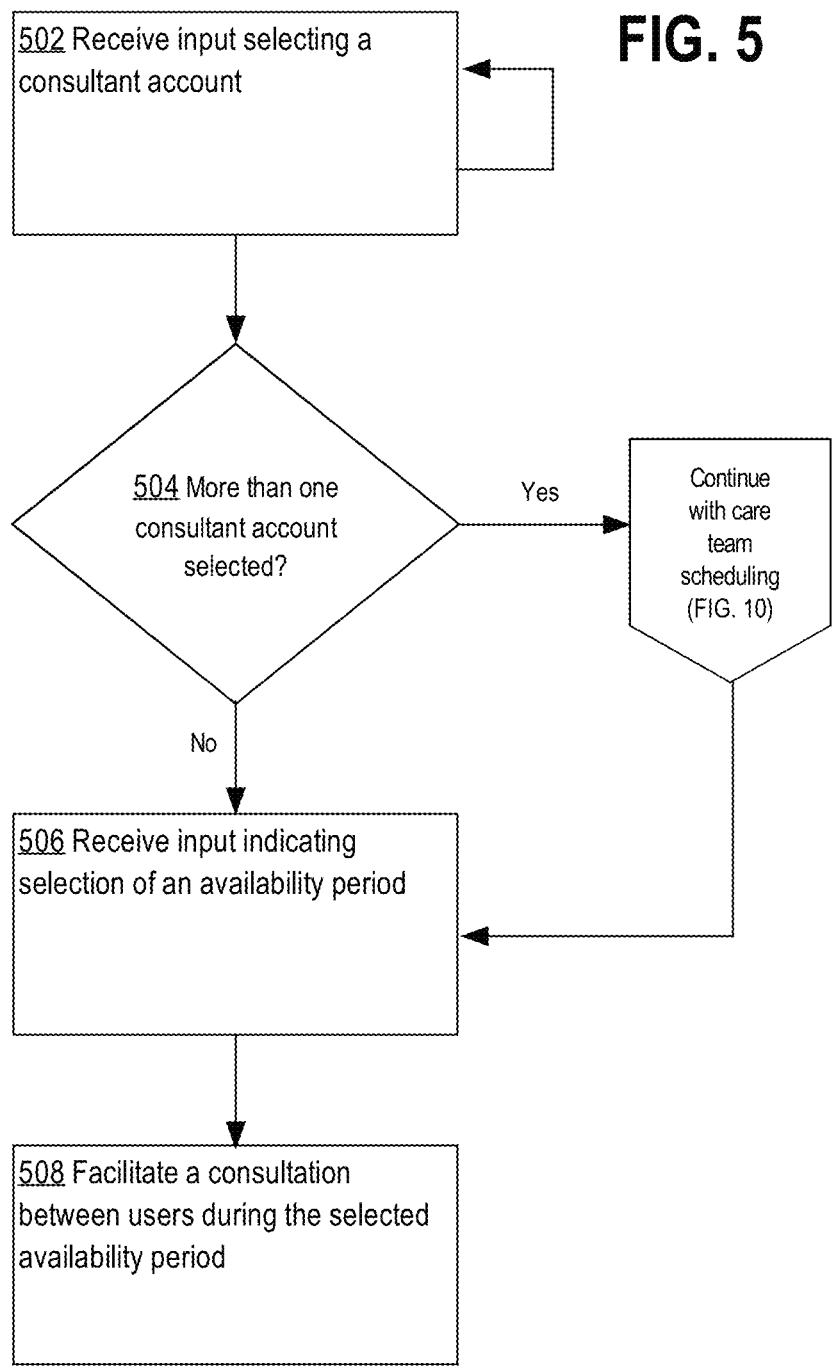

COMPUTER-BASED METHOD AND SYSTEM FOR FACILITATING VOICE CONSULTATIONS

BENEFIT CLAIM/PRIORITY INFORMATION

This application claims the benefit under 35 U.S.C. § 120 as a Continuation-in-part of application Ser. No. 13/922,394, filed Jun. 20, 2013, which claims the benefit under 35. U.S.C. § 119(e) of provisional application 61/661,904, filed Jun. 20, 2012, and provisional application 61/754,817, filed Jan. 21, 2013, the entire contents of which are incorporated by reference as if fully set forth herein. The applicant(s) hereby rescind any disclaimer of claim scope in the parent application(s) or the prosecution history thereof and advise the USPTO that the claims in this application may be broader than any claim in the parent application(s).

TECHNICAL FIELD

The present disclosure relates generally to a computer-implemented process for facilitating efficient collaboration among physicians and other healthcare participants. The disclosure relates more specifically to a networked, cloud-based management computer system that enables users to establish direct communications with other users for the purposes of collaborating on issues related to providing medical care.

BACKGROUND

The approaches described in this section could be pursued, but are not necessarily approaches that have been previously conceived or pursued. Therefore, unless otherwise indicated herein, the approaches described in this section are not prior art to the claims in this application and are not admitted to be prior art by inclusion in this section.

Physicians and other healthcare providers often find the need or desire to communicate among one another in the course of providing medical care. For example, physicians may desire to communicate with one another to obtain information about medical questions or issues that are outside of a physician's area of expertise, to discuss issues related to a mutual patient, or to refer a new patient. In general, communication among physicians and other healthcare providers is an important tool for providing well-rounded care for patients.

Currently, physicians may attempt to discuss medical issues with another by meeting informally during the physicians' daily rounds at a hospital or by attempting to call or email one another. However, physicians are typically under tremendous time pressure to see patients, answer phone calls, review test results, etc., and finding a mutually available time for two or more physicians to collaborate about a particular issue is often difficult. As a result, attempts by one physician to reach another physician may often result in message taking, phone calls back and forth, and other delays in making contact that make the collaboration process highly inefficient.

Furthermore, with an increasing amount of specialization and sub-specialization among those practicing medicine, finding the most appropriate person to answer a particular question may be challenging. For example, a physician seeking advice on a particular medical issue may not be personally acquainted with another physician with the appropriate expertise and that is able to readily discuss the issue.

Another issue facing physicians today is an increased focus in the medical community on evidence-based best practices including the use of various guidelines and other medical references developed by expert consensus within each medical specialty. While these resources are becoming increasingly accessible online to physicians, the proliferation of these resources often makes it difficult for physicians to determine which resources may be the most relevant and up-to-date when information is needed, especially in practice areas outside of a physician's own area of expertise.

BRIEF DESCRIPTION OF THE DRAWINGS

In the drawings:

FIG. 5 illustrates a computer-implemented process for facilitating a consultation between two or more users in accordance with an embodiment.

DETAILED DESCRIPTION

Figure 1:
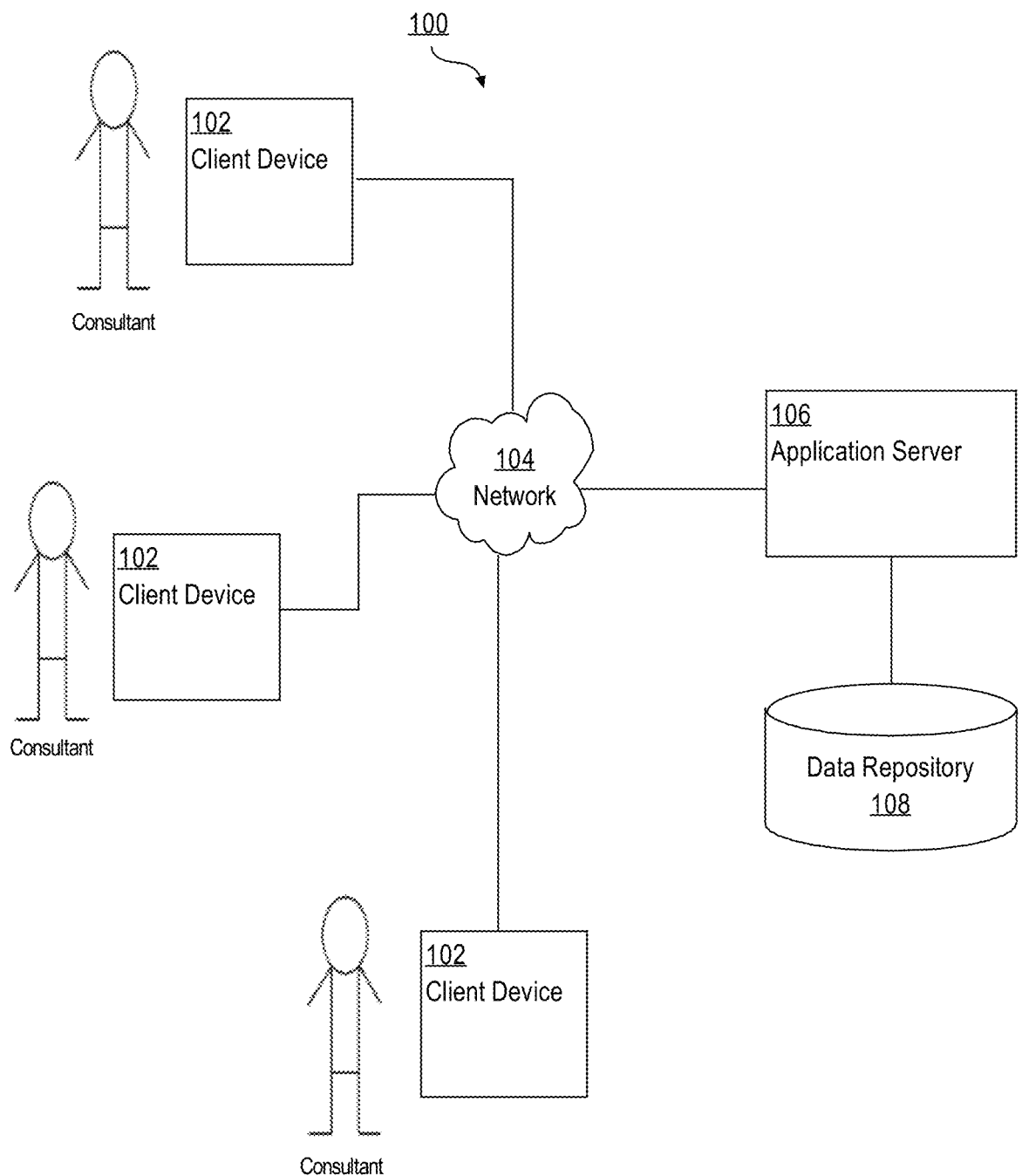
FIG. 1 illustrates an example networked computer system arrangement that may be used to implement an embodiment.

In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Embodiments are described herein according to the following outline:

1.0 General Overview
2.0 Structural Overview
3.0 Functional Overview
   3.1 Consultant Registration
   3.2 Consultant Networks
   3.3 Consultant Availability Scheduling
   3.4 Conducting Consultations
      3.4.1 Consultant Searching
      3.4.2 Care Team Scheduling
      3.4.3 Establishing a Consultation
      3.4.4 Reference Bookmarking
   3.5 Post-Consultation
4.0 Implementation Mechanism—Hardware Overview 1.0 General Overview In an embodiment, the disclosure provides a software tool that supports both fixed and mobile voice communications between team members and is programmed to inspect the respective calendars of two or more members wishing to coordinate, to schedule a mutually convenient time for the voice call, to notify the respective participants of the time of the scheduled call, to alert participants just prior to the call, and to automatically initiate said coordinating voice call. Embodiments may be programmed to keep a log of call completion status, call duration and call participants.

In another embodiment, the disclosure provides a software tool that helps find the most appropriate consultant in any given situation and adds appropriate digital information attachments to the call.

According to various embodiments, a healthcare collaboration computer system, computer program, and computer-implemented methods are provided to enable physicians and other participants in the healthcare system to efficiently collaborate with one another by engaging in system-facilitated consultations. As used herein, a consultation may generally refer to communications established between two or more users of the healthcare collaboration system. In general, the system and methods described herein provide the ability for users to establish consultations with other users at a mutually convenient time, whether or not there exists a prior relationship between the users. In exchange for time spent conducting consultations, users may be compensated using any number of compensation methods. By providing a platform that facilitates communication and collaboration among healthcare participants, both patients and physicians are benefited by improving the efficiency of medical diagnosis and treatment, thereby increasing satisfaction and lowering costs of the healthcare system.

According to one embodiment, a computer-implemented method comprises receiving first input specifying an availability schedule of a first user, wherein the availability schedule indicates one or more availability periods; receiving second input specifying, for at least one of the one or more availability periods, one or more consultation types of a set of consultation types; storing, in a data repository, the availability schedule in association with a consultant record representing the first user.

According to another embodiment, a computer-implemented method comprises receiving, from a device associated with a first user, input specifying two or more second users, wherein each of the two or more second users is associated with a particular availability schedule, and wherein each of the particular availability schedules specifies one or more particular availability periods; retrieving, for each second user of the two or more second users, the particular availability schedule associated with said each second user; generating, based on the retrieved particular availability schedules, one or more team availability periods, wherein each team availability period of the one or more team availability periods indicates a particular availability period that is present in the particular availability schedule of said each second user; receiving input selecting a particular team availability period of the one or more team availability periods; storing, in a data repository, a consultation appointment based on the particular team availability period.

According to yet another embodiment, a computer-implemented method comprises receiving a first request to store information associated with a web-accessible medical reference; receiving a second request to associate the information with a consultation record, wherein the consultation record represents an occurrence of a consultation between two or more or more healthcare consultants; in response to receiving the second request, storing, in a data repository, a link between the consultation record and the information associated with the medical reference.

Other embodiments include, without limitation, a non-transitory computer-readable medium that includes processor-executable instructions that enable a processing unit to implement one or more aspects of the disclosed methods as well as a system configured to implement one or more aspects of the disclosed methods.

2.0 Structural Overview

FIG. 1 illustrates a networked computer system arrangement that may be used to implement an embodiment. In an embodiment, the computer system generally comprises one or more client computing devices (client devices) 102, a network 104, at least one application server computer (server) 106, and a data repository 108.

In an embodiment, each of client devices 102 comprises a smartphone, tablet computer, netbook computer, laptop computer, desktop computer, or other computing device. Examples of client devices 102 include APPLE IPHONE and IPAD devices, ANDROID devices, and other laptop and desktop computing devices. In general, a client device 102 may be associated with a user, also referred to herein as a consultant, of the networked computer system. Each of the users depicted in FIG. 1, and the client devices 102 depicted in association with each of the users, may be located practically anywhere at any given time. For example, the users may include physicians, nurses, medical school faculty, and other users located in various offices or hospitals in the same area or located across different areas of the country and the world.

Typically, one or more wired and/or wireless links couple the client devices 102 to network 104, which broadly represents one or more local area networks, wide area networks, internetworks, global interconnected internetworks such as the public internet, or a combination thereof. For the purposes of illustrating a clear example, three client devices 102 are shown in FIG. 1 and one cloud symbol representing network 104 is shown, but practical implementations may use thousands of client devices and any number of interconnected networks.

In an embodiment, application server 106 comprises a collection of applications and modules associated with hosting a healthcare collaboration platform, as described in more detail herein. In general, the applications and modules of application server 106 are configured to enable users to access and interact with the healthcare collaboration system via one or more client devices 102.

In one embodiment, application server 106 comprises an HTTP server that is configured to dynamically form and server HTML documents or other web content to browsers at client devices 102 as part of delivering information services to the computers. In an embodiment, the HTTP server and generated HTML documents and other web content may be accessed from client devices 102 using an HTTP browser to receive web pages or other screens. For example, the application server 106 may be configured to provide a World Wide Web-based management interface, or portal, that enables consultants and other users to securely access, view, and configure various aspects of the system.

In an embodiment, data repository 108 generally represents any data storage device that may be configured to store data (e.g., local memory on application server 106, shared memory, multiple servers connected over the internet, systems within a local area network, etc.). Various elements or portions of data stored in the data repository 108 may be distributed and stored in multiple data repositories (e.g., servers across the world). In one or more embodiments of the invention, the data repository 108 includes flat, hierarchical, network based, relational, dimensional, object modeled, or data files structured otherwise. For example, data repository 108 may be maintained as tables of an SQL database.

Figure 2:
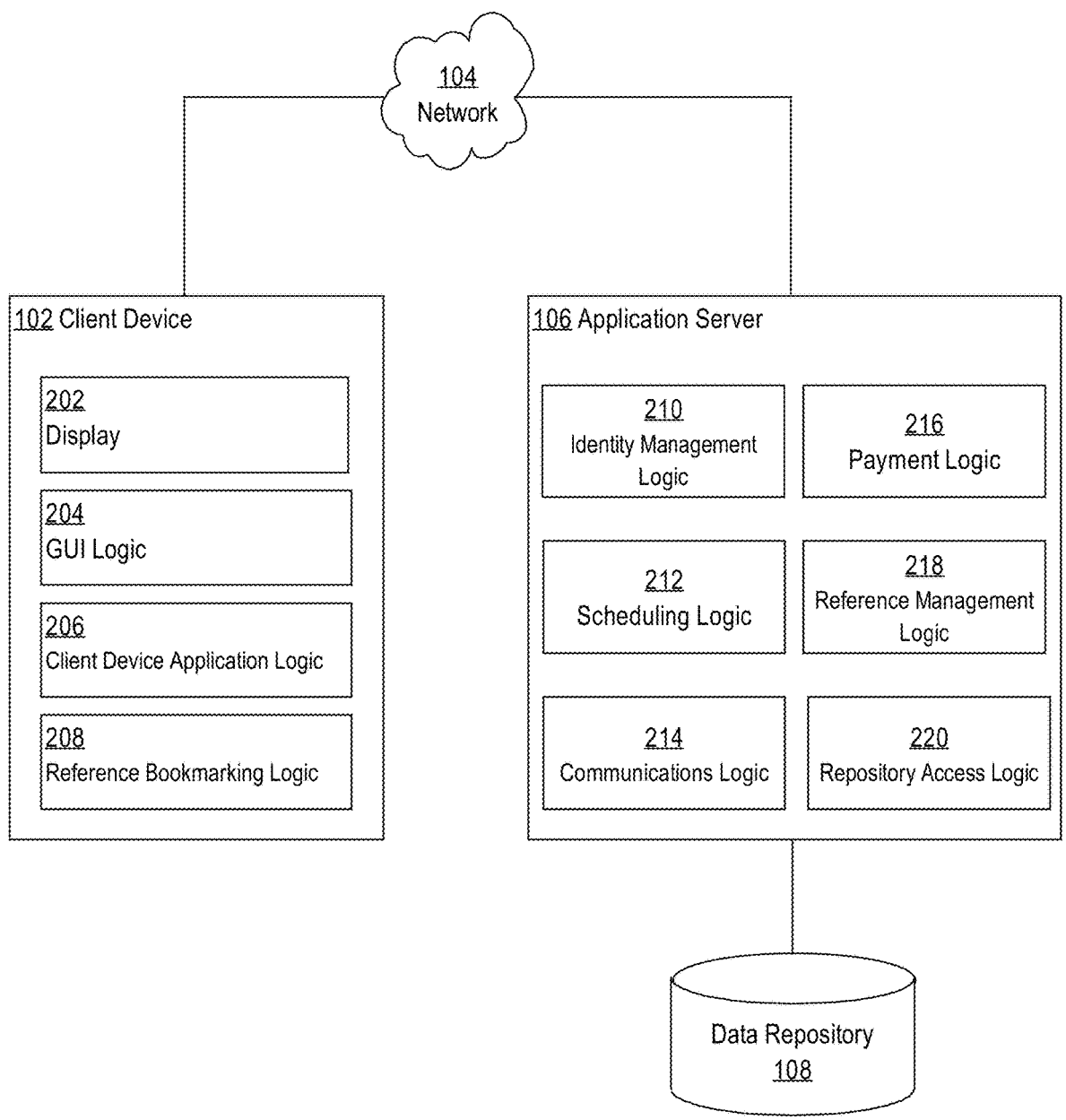
FIG. 2 illustrates further details of an embodiment of the system of FIG. 1.

FIG. 2 illustrates further details of an embodiment of the system of FIG. 1. In an embodiment, a client device 102 includes a display 202, graphical user interface (GUI) logic 204, client device application logic 206, and bookmarking logic 208, each of which may comprise one or more elements of firmware, hardware, software, or a combination thereof in various embodiments that can implement the functions described herein. Logical elements shown in FIG. 2 may be integrated into a single application program or app that executes under control of an operating system in the client device 102. In some embodiments, the functions described herein for logic 204, 206, 208 may be implemented in browser-executable script code or other client-side executable code that executes in a browser or other element of the client device 102; in other words, local executable logic or an app, separate from a browser, is not required.

In an embodiment, GUI logic 204 may be a set of program instructions which, when executed by one or more processors of a client device 102, are operable to receive user input and to display a graphical representation of one or more graphic constructs related to the healthcare collaboration system approaches described herein. As one example, a client device 102 may be a smartphone or tablet and GUI logic 204 may be operable to receive touch screen signals and other user input from, and display the graphic constructs to, a graphical user interface that is provided on display 202. Touch screen signals may comprise selecting buttons, holding down buttons, selecting items displayed on the screen, dragging, or other gestures or selections. In general, GUI logic 204 is configured to receive user input and determine what user requests or commands are represented by the user input.

In an embodiment, client device application logic 206 is configured for enabling user access to and interaction with the healthcare collaboration system provided by an application server 106 and performing other functions described herein. In one embodiment, client device application logic 206 may be implemented as part of an application program or app configured to execute on the iOS or Android operating system. In other embodiments, client device application logic 206 may be implemented as a combination of programming instructions written in any programming language (e.g., C++ or Java) and hardware components (e.g. memory, CPU time) that have been allocated for executing the program instructions on a client device 102.

A client device 102 may further comprise reference bookmarking logic 208 that is configured to enable users of a client device 102 to add, categorize, and share web-based medical reference materials with other users. In one embodiment, reference bookmarking logic 208 may be logic that operates as part of a web browser running on a client device 102. For example, reference bookmarking logic 208 may be implemented as a "bookmarklet" that includes commands in a scripting language (e.g., JavaScript) and that is configured to enable a user to capture information related to a web page or other web browser-accessible resource and to send the information to an application server 106 for storage. The use of medical references is not required, and in some embodiments, technical reference materials or other non-medical, non-technical reference materials may be identified and shared in the same manner described above for medical references.

In an embodiment, application server 106 generally may include functionality to receive data from client devices 102 including information relating to consultant availability schedules, bookmarked references, and other information, to store the data in a data repository 108, and to facilitate consultations between users. In one embodiment, an application server 106 comprises identity management logic 210, scheduling logic 212, communications logic 214, payment logic 216, reference management logic 218, and repository access logic 220.

In an embodiment, identity management logic 210 provides processes for verifying the identity of users desiring to register with the healthcare collaboration system and for authenticating registered users requesting access to the system. For example, identity management logic 210 may be configured to receive user input and to verify medical licensure information, employment information, and any other information related to the identity of a user requesting registration with the system. In an embodiment, identity management logic 210 may be configured to interface with one or more external systems and data sources to assist in verifying a user's provided information. Identity management logic 210 may also be configured for generating user account information such as usernames and passwords and for authenticating user account login requests.

Application server 106 may further comprise scheduling logic 212 that is configured to receive and store user-specified availability schedules for consultations, as described further herein. In one embodiment, scheduling logic 212 may store the consultation availability schedules in a data repository 108 or may interface with a hosted calendar resource for the storage of availability schedules.

In an embodiment, communications logic 213 may comprise a set of instructions which, when executed by one or more processors, are operable to facilitate communications between two or more users for the purposes of conducting a consultation or other purposes. For example, communications logic 213 may be configured to establish a phone, video conferencing, online chat, or communications between two or more client devices 102 in response to a user associated with a first client device scheduling a consultation with one or more other users associated with other client devices.

In an embodiment, payment logic 216 provides processes for automating payments to users for time spent conducting consultations with other users. For example, payment logic 216 may comprise logic for integrating with one or more Automated Clearing House (ACH) vendors to process payments to users. In an embodiment, payment logic 216 may further comprise logic for determining payment amounts based on tracking the time users spend conducting consultations and other information, as described further herein.

In an embodiment, document management logic 218 may comprise a set of instructions which, when executed by one or more processors, are operable to receive, store, and manage information relating to web-accessible reference materials. For example, document management logic 218 may be configured to perform processes related to receiving requests from client devices 102 specifying information related to a web-based medical resource, storing the information, and associating the information with stored representations of consultations.

In an embodiment, application server 106 comprises repository access logic 220. Repository access logic 220 may comprise a set of instructions which, when executed by one or more processors, are operable to access and retrieve data from data repository 108.

3.0 Functional Overview

For the purposes of illustrating how the functions described herein operate, the following sections describe example graphical user interface (GUI) displays for the described healthcare collaboration system features. However, the GUI displays described herein represent only selected examples of visualizations for the healthcare collaboration system operations that are described herein. Thus, the disclosure broadly encompasses any methods of operating a healthcare collaboration system that are described herein.

Further, no particular GUI is required and the disclosure is intended to encompass processing approaches for the healthcare collaboration system independent of any GUI, and it is not intended to be limited to any particular GUI or other form of display. For example, the example graphical user interfaces merely represent one way for a user to register with the system as a consultant, to specify a user's availability schedule, and to search for other users for the purposes of establishing a consultation; in other embodiments, programmatic methods may be used to obtain the same information and other forms of data output may be used such as logging, reporting, storing in database tables, storing in spreadsheets, etc.

3.1 Consultant Registration

In an embodiment, users may request registration with the healthcare collaboration system in order to participate as a "consultant" in the system. As used herein, a consultant generally refers to any user of the healthcare collaboration system, whether or not the user desires to request the consultation services of other users, to be requested for his or her consultation services, or to perform other functions. In general, registering a user to participate as a consultant may comprise receiving user input identifying the user as a healthcare system participant (e.g., a physician, nurse, medical school faculty member, or drug company representative), verifying the identity and qualifications of the user based on the received user input, and creating a consultant account for the user. Certain embodiments herein are described in connection with healthcare consultations, but the same computing elements, structure and data processing functions may be used in fields other than healthcare, and interoperation with healthcare consultants is not required. Users may come from any industrial, technical or commercial field including but not limited to accounting or finance, education, business consulting, law, engineering, journalism, government or politics, and so forth.

In an embodiment, a user may request registration with the healthcare collaboration system by using a web page generated by an application server 106 and displayed on a client device 102, by using one or more screens of an application running on a client device 102, or using any other user registration mechanism. For example, a registration webpage accessed by a user and displayed on a client device 102 may prompt the user to provide one or more items of information including a desired user name and password and other information about the user including the user's name, an address, the user's current place of employment, etc. The provided information may be used by an application server 106 in the creation of a consultant account in the system for that user.

In an embodiment, user registration may comprise one or more steps of user identity verification and management. For example, it may be desired that only persons who are currently licensed and in good standing with an appropriate medical board be allowed to use the system as an active consultant. Thus, in an embodiment, a user may be prompted to provide one or more items of information related to the user's medical license status. The provided medical license status information may be used to search one or more internal or external data sources in order to verify the identity and current licensure status of the user requesting registration with the system. The verification process may comprise other steps including determining whether any malpractice or ethical complaints are associated with the user. The licensure status information of registered users may be re-assessed periodically, for example, on an annual basis, in order to monitor systems users for ongoing licensure.

In an embodiment, a verified user may be associated with a consultant account stored in a data repository 108. During the registration process or in subsequent configuration steps, a user may provide additional information to store in association with the user's consultant account. For example, a user may provide input specifying one or more medical specialties of the user, the user's educational and residency background information, the user's current practice location and address, a profile picture, etc. In an embodiment, the provided information may be stored in association with the user's consultant account and displayed in various screens of the system as part of the user's consultant account profile, as further described herein.

In one embodiment, the additional information provided by a user may include one or more telephone numbers associated with the user. In general, the telephone numbers may correspond to particular communication devices at which the consultant desires to be contacted by other system users for consultations and other system functions. The communication devices may, for example, be a client device 102 such as a smartphone, or may be a traditional landline phone or other communication devices. For example, a user may provide both a first phone number that is associated with the user's smartphone and a second phone number that is associated with the user's landline phone at home. In general, a user may register any number of phone numbers with the system. For example, one or more phone numbers registered by a particular user may be configured as primary phone numbers for establishing communications with the user, while one or more other phone numbers may be configured as back-up phone numbers for use if the system is unable to establish communications with user using one of the primary phones numbers.

In an embodiment, in response to receiving user input specifying a phone number to associate with the user's consultant account, an application server 106 may send a text message, automated voice message, or other confirmation message to the device associated with the phone number in order to confirm that the phone number is associated with the user. An application server 106, for example, may store the phone number in association with the user's consultant account only after receiving a confirmation message back from the device.

3.2 Consultant Networks

In an embodiment, a created consultant account may be associated with one or more consultant networks. In this context, a consultant network generally refers to a logical grouping of consultant accounts for the purpose of assisting user searches for consultants and other processes described herein. A particular consultant network may be based, for example, on a geographical area of practice, a place of employment, a practice specialty, or any other characteristic shared by two or more users. Example consultant networks that a consultant account may be associated with include a local hospital network, a national network, a multi-specialty medical group network, etc.

In one embodiment, a consultant account may be associated with one or more consultant networks based on information provided by the user associated with the consultant account during the registration process or in subsequent configuration steps. For example, during the registration process, a user may provide information indicating a particular hospital or geographic location where the user is currently employed. Based on the provided employment information, a consultant account for the user may be associated in a data repository with a "local" consultant network that includes consultant accounts of other users employed by the same hospital and by other hospitals in the same local area. As another example, a user may provide information during the registration process identifying the user as a faculty member at a medical school. Based on the provided information identifying the user as a medical school faculty member, a consultant account for the user may be associated with a more general "national network" and/or a more specific "medical school faculty" network. The consultant networks identified above are provided only as examples and a consultant account generally may be associated with any number and type of consultant networks as provided by the system.

In one embodiment, a user may further define one or more custom or "ad-hoc" consultant networks in addition to the consultant networks provided by the system. For example, a physician user may frequently interact with a particular group of cross-specialty physicians for issues outside of the physician's area of expertise or with a group of physicians that are each working with a mutual patient. In an embodiment, the user may specify the creation of one or more custom consultant networks by providing a label or other identifier for the custom network and further providing input specifying one or more other consultant accounts to add to the custom consultant network. A custom consultant network may be visible only to the user creating the network or to other specified users in the system.

3.3 Consultant Availability Scheduling

In an embodiment, a user may provide input indicating the user's availability for participation in consultations with other users in the system. The input may specify time periods during which the user desires to receive consultation communications from other users in the system. For example, a user may generally be unavailable to discuss issues with other users during the user's daily office hours, but may generally be available to communicate with other users during night and weekend hours. In an embodiment, a user may provide this information to the healthcare collaboration system so that others may view the user's availability schedule and schedule consultations during the user's preferred availability periods.

In one embodiment, input may be received specifying a user's availability schedule including one or more availability periods. For example, a user may provide input specifying an availability schedule in the form of a calendar-based schedule of the user's availability. The calendar-based schedule may specify one or more availability periods indicating particular blocks of time on a weekly or other basis during which the user is available to receive consultation communications from other users.

In an embodiment, a user may further specify one or more consultation types to associate with each availability period. The consultation types generally may represent particular types of consultation communications that the user desires to receive during a particular availability period. Example consultation types include an informational consultation, mutual patient consultation, new patient consultation, etc. For example, an informational consultation may represent a consultation that does not involve any sharing of specific patient information or intent for a specific diagnosis or treatment information. As another example, a mutual patient consultation may represent a discussion relating to a mutual patient. A new patient consultation may represent a consultation in which a physician is referring a patient to another physician. By associating one or more consultation types with particular availability periods, a user may indicate what types of consultations the user desires to receive on a per availability period basis. For example, a user may desire to participate in mutual patient and new patient consultations only during the user's office hours. Similarly, a user may desire to participate in informational consultations only during weekend hours.

Figure 3:
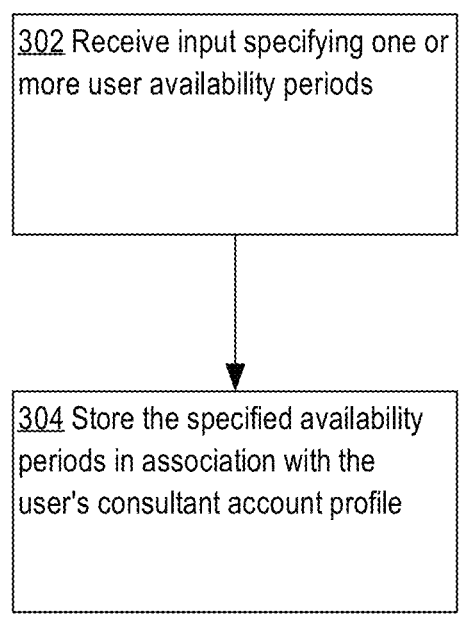
FIG. 3 illustrates a computer-implemented process for generating a user's consultation availability schedule in accordance with an embodiment.

FIG. 3 illustrates a computer-implemented process for generating a user's consultation availability schedule. In Step 302, input is received specifying one or more user availability periods. In one embodiment, the input specifying one or more availability periods may indicate, for one or more days of the week, time periods during which a user generally is available to receive consultation communications. For example, a user may provide input specifying that each Monday the user is available from 1 PM to 2 PM and from 7 PM to 10 PM and each Tuesday from 8 AM to 11 AM. In another embodiment, a user may provide input specifying availability periods for a particular calendar days. For example, a user may provide input specifying the user's availability on Aug. 1, 2013 from 8 AM to 9 PM, on August 3 from 8 AM to 11 AM, etc.

Figure 4A:
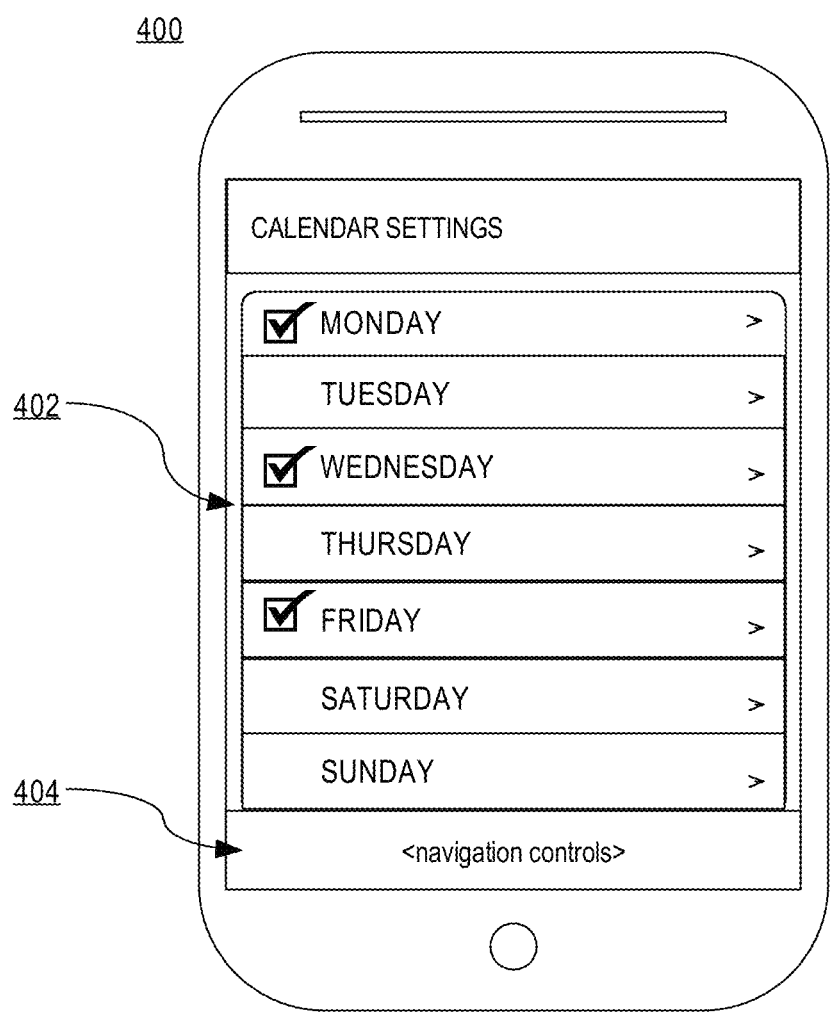
FIG. 4A, FIG. 4B illustrate example graphical user interfaces that are configured to enable a user to specify an availability schedule.
Figure 4B:
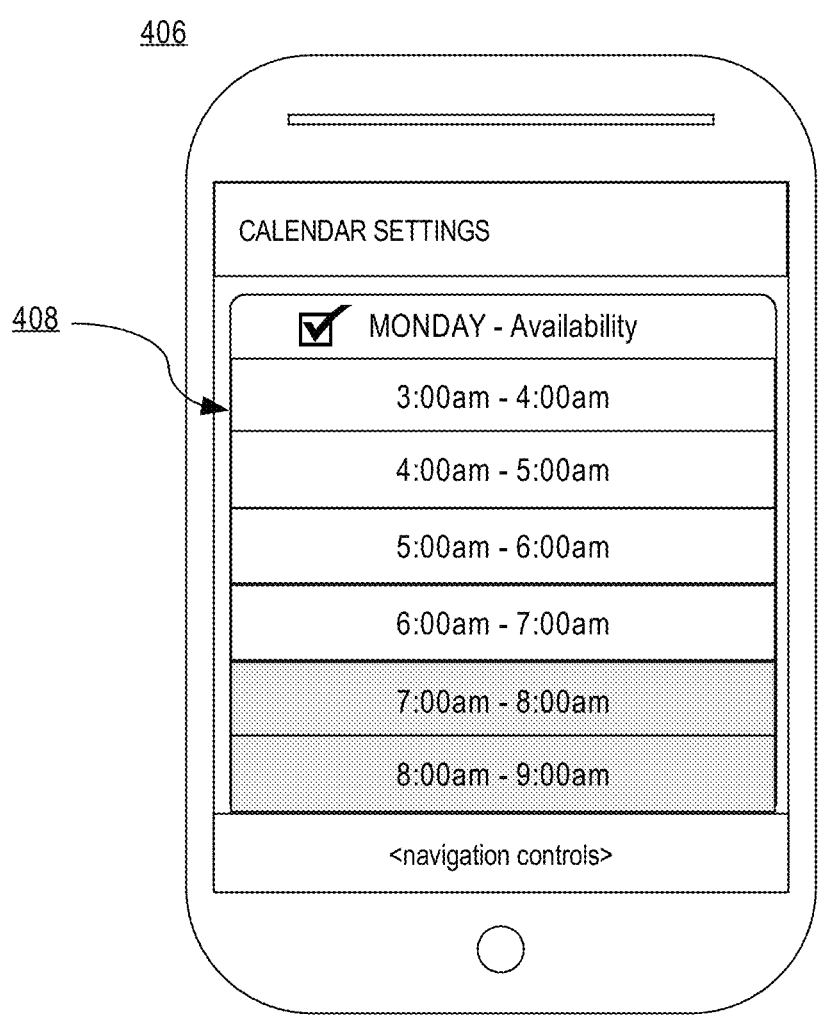

FIGS. 4A, 4B illustrate example graphical user interfaces that are configured to enable a user to specify an availability schedule. For example, FIG. 4A illustrates a GUI 400 that may be displayed on a client device 102 and that is configured to enable a user to select one or more days of the week and to specify one or more availability periods for the selected days of the week. In an embodiment, GUI 400A comprises button area 402 and navigation control area 404.

In an embodiment, button area 402 enables a user to select one or more particular days of the week for which to specify availability periods. For example, if a user desires to indicate a particular availability period the user has on Mondays, the user may select the button labeled "Monday" to cause display of a screen for specifying the availability periods. In an embodiment, depending on whether a user has specified any availability periods for a particular day, the display of the buttons in button area 402 may change, for example, to display a checkbox for days with specified availability periods, as depicted in FIG. 4A.

In an embodiment, navigation control area 404 generally represents one or more buttons or other interface elements that enable a user to navigate the various screens of a GUI 400. For example, navigation control area 404 may comprise one or more of a "back" button configured to cause display of the previously viewed screen, a "home" button configured to cause display a home page for the application, and a "settings" button configured to cause display of a screen that enables the user to configure one or more application configuration settings.

FIG. 4B illustrates a GUI 406 that is configured to enable a user to select one or more availability periods for a particular day selected in FIG. 4A. In an embodiment, FIG. 4B comprises a button area 408 including one or more selectable availability period buttons each corresponding to a particular availability period for the day of the week selected in FIG. 4A. In an embodiment, a user may initially be unavailable during all availability periods, available during all availability periods, or available during certain availability periods (e.g., from 9 AM to 5 PM on Monday through Friday). A user may toggle the user's availability for one or more availability periods, for example, by selecting a button corresponding to the desired availability period in button area 408. In response to a user's selection of a particular availability period, the display of the corresponding button may change to indicate the selection, for example, by changing color or shading. After a user has selected any desired availability time periods, the user may select input an input mechanism to save the user's selections or the user's selections may be saved automatically without further input from the user.

As described above, availability periods selected by a user may be associated with one or more consultation types. In one embodiment, a user may specify one or more particular consultation types for a selected availability period by selecting the availability period in button area 402 and providing further input to a consultation type selection screen (not displayed) or using any other interface mechanism.

Referring again to FIG. 3, in Step 304, a user specified availability schedule is stored in association with the user's consultant account profile. For example, the user's availability schedule may be stored in data repository 108 or using an external calendar service.

3.4 Conducting Consultations

FIG. 5 illustrates a computer-implemented process for establishing a consultation between two or more users. In general, a user may establish a consultation with another user by searching for and selecting one or more consultant accounts, and selecting a particular availability time for the one or more consultant accounts. In an embodiment, one or more of the steps below may be omitted, repeated, or performed in a different order. The specific arrangement shown in FIG. 5 is not required.

3.4.1 Consultant Searching

In Step 502, input is received selecting a consultant account. For example, a user may select a particular consultant account because the user desires to establish a consultation with the user associated with the consultant account. In one embodiment, a user may select a particular consultant account by performing a search for the consultant account based on any number of criteria including, for example, the name of the user associated with the consultant account, a particular consultant network, or a practice specialty of the user associated with the consultant account.

Figure 6A:
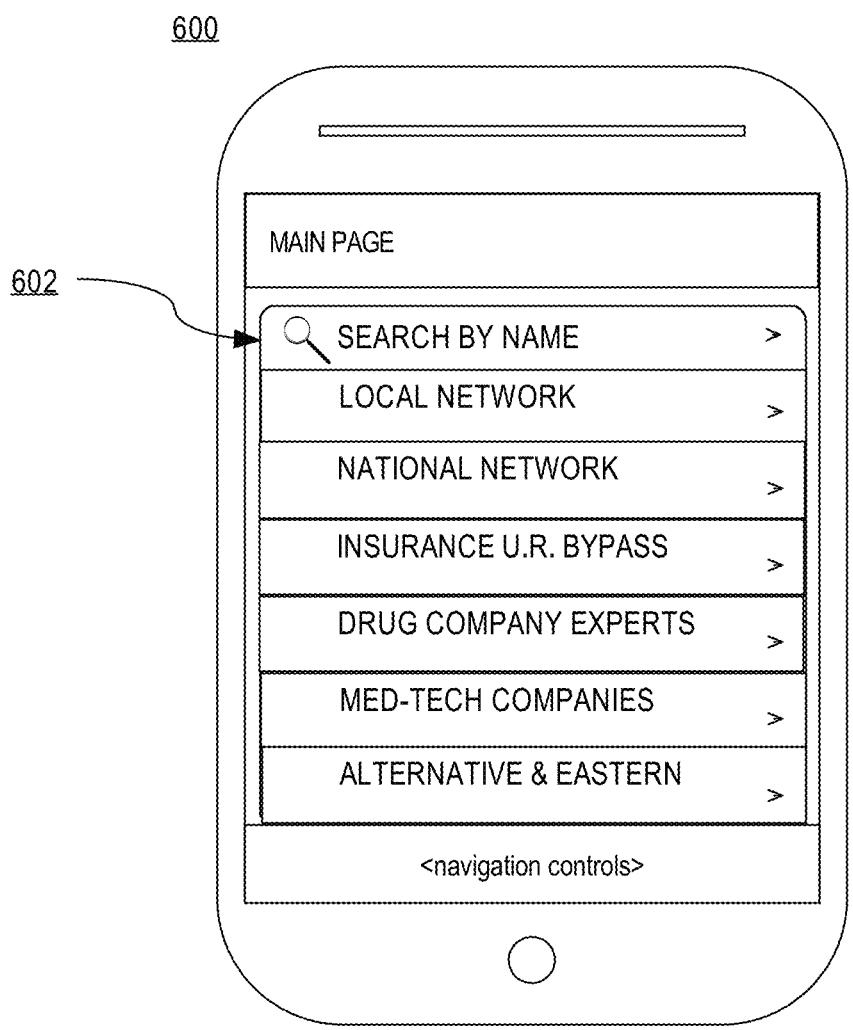
FIG. 6A, 6B, 6C illustrate example graphical user interfaces that are configured to enable a user to search for consultants.
Figure 6B:
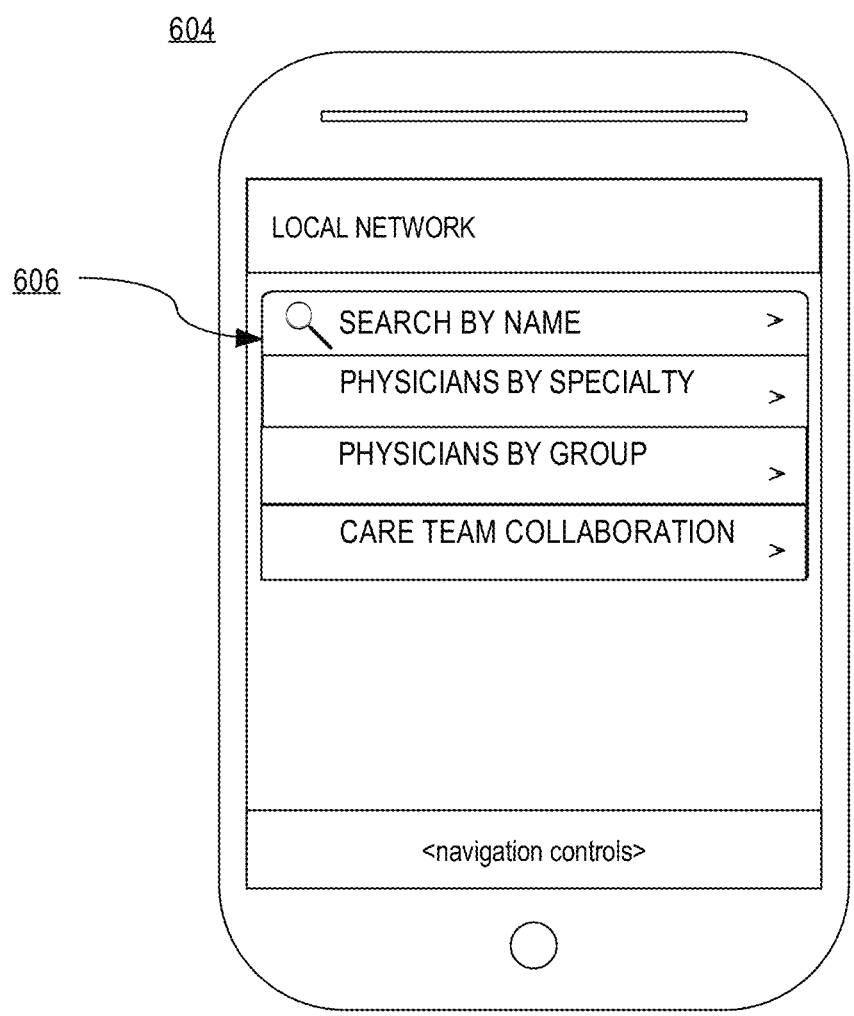
Figure 6C:
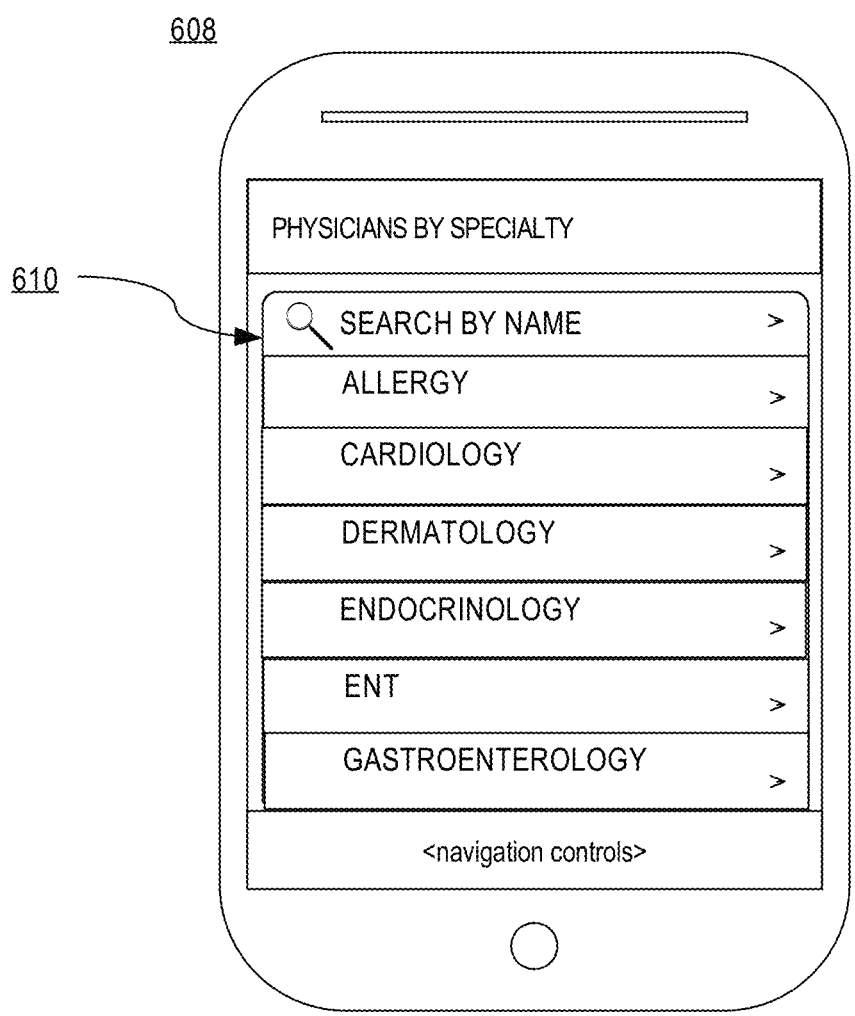

FIG. 6A, 6B, 6C illustrate example graphical user interfaces that are configured to enable a user to search for consultant accounts. In an embodiment, GUI 600 comprises consultant search buttons 602. In general, consultant search buttons 602 are configured to provide a user a variety of ways to search for consultant accounts including searching for a consultant account by name or by a particular consultant network (e.g., a local network, a national network, or a drug company network). For example, in response to a user selection of the search button labeled "Search By Name," the user may be presented with a text box or other interface element enabling the user to type in the name or a portion of the name. As another example, a user may select one of the buttons labeled "Local Network" or "National Network" in consultant search buttons 602 to narrow down the user's search to particular consultant networks.

FIG. 6B illustrates a GUI 604 that may be displayed in response to a user selecting one of the buttons from GUI 600 to narrow the consultant's search to a particular consultant network or category. For example, GUI 604 illustrates a display screen that may be generated in response to a user selecting the button labeled "Local Network" in FIG. 6A. In an embodiment, GUI 604 comprises buttons 606 that enable a user to further narrow the user's search to consultants grouped by specialty, by group (e.g., a pre-defined or custom group of consultant accounts), or to specify multiple consultant accounts for a care team consultation, further described in a separate section below.

FIG. 6C illustrates a GUI 608 that may be displayed in response to a user's selection of a button from GUI 600. For example, GUI 608 may be displayed in response to a user selecting the button labeled "Physicians By Specialty" in FIG. 6B. In an embodiment, GUI 608 comprises specialty buttons 610. In response to a user selecting a button from specialty buttons 610, the user may be presented with another screen displaying one or more sub-specialties, or the user may be presented with a screen displaying a list of consultant accounts associated with the selected specialty. In an embodiment, a user may select a listed consultant account to cause display of a consultant account profile for the particular consultant account.

Figure 7:
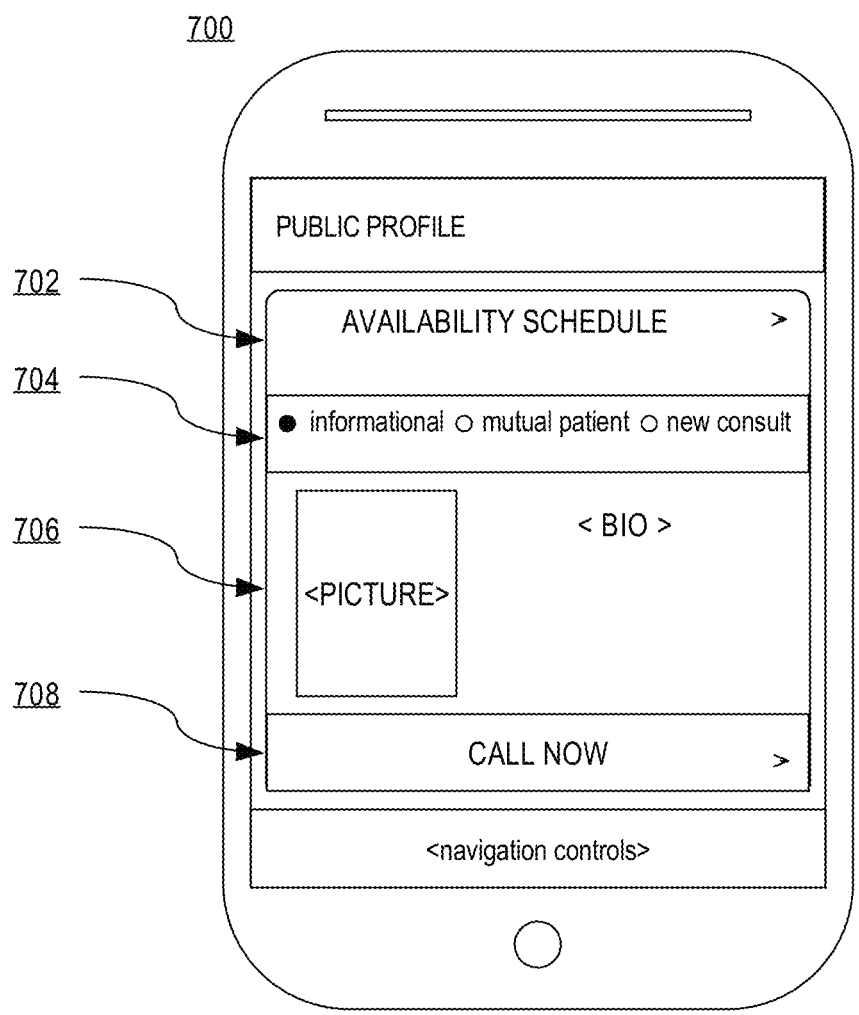
FIG. 7 illustrates an example graphical user interface displaying a user's consultant account profile and availability schedule information.

FIG. 7 illustrates a graphical user interface displaying a consultant account profile for a particular consultant account. For example, the consultant account profile may be displayed in response to a user selecting a particular consultant account based on a consultant account search, as described above. In an embodiment, GUI 700 comprises availability schedule button 702, consultation type buttons 704, profile information 706, and consultation call button 708.

In an embodiment, availability schedule button 702 is configured to enable a user to view the availability schedule associated with the displayed consultant account profile. For example, in response to user selection of schedule button 702, a daily, weekly, monthly or other calendar-based view of the availability schedule may be presented to the user, enabling the identification of availability periods during which the user associated with the consultant account profile is available to participate in consultations. In an embodiment, a displayed availability schedule may further include information about particular consultation types that the user associated with the consultant account profile has specified during particular availability periods. For example, one displayed availability period may indicate that the user associated with the consultant account profile is available only for mutual patient and new patient consultations, while another availability period may indicate that the user is available for informational consultations at during that time.

In an embodiment, consultation type buttons 704 include one or more interface elements that enable a user to indicate a type of consultation the user desires to participate in with the user associated with the consultant account profile. For example, a user may select the button labeled "informational" to indicate that the user desires to establish an informational consultation with the user associated with the profile. The selection of a particular consultation type may determine the current availability of the user associated with the consultant account profile, as further described below.

In an embodiment, profile information 706 comprises information about the user associated with the consultant account profile. For example, the information displayed in profile information 706 may include information received from the user during the registration process or in subsequent configuration steps including a profile picture of the user, the user's educational background, areas of practice, etc.

In an embodiment, consultation call button 708 may be configured to cause the system to facilitate a consultation with the user associated with the consultant account profile depending on the user's availability schedule. In an embodiment, based on the current time and a selection of a consultation type from consultation type buttons 704, a current availability status of the user associated with the consultant account profile may be determined. For example, assume the current time is 10:30 AM on a Thursday and a first user desires to establish an informational consultation with a second user associated with the consultant account profile displayed in FIG. 7. In the example, the first user may select the informational button from consultation type buttons 704 to indicate the desired type of consultation. In response to the current time and the consultation type selection, it may be determined whether the availability schedule for the displayed consultant account profile includes an availability period that overlaps with the current time and that is associated with the specified consultation type. If there exists a current availability time associated with the specified consultation type, the first user may initiate a consultation with the second user by selecting consultation call button 708. In an embodiment, by selecting consultation call button 708, a request may be sent to application server 106 to facilitate a consultation between the users. The process of establishing a consultation between two or more users is further described in a separate section below.

In an embodiment, one or more display characteristics of the consultation call button 708 may change depending on the current time, a selection of a consultation type, and the availability schedule of the user associated with the displayed consultant account profile. For example, based on the current time, a selected consultation type, and the associated availability schedule, if the user associated with the consultant account profile is currently available to participate in an informational consultation, consultation call button 708 may be display a green color. Alternatively, if the consultation type button labeled "mutual patient" is selected and, based on the associated availability schedule, the user associated with the consultant account profile is not currently available to participate in mutual patient consultations, the consultation call button 708 may display a red color or be disabled.

Figure 8:
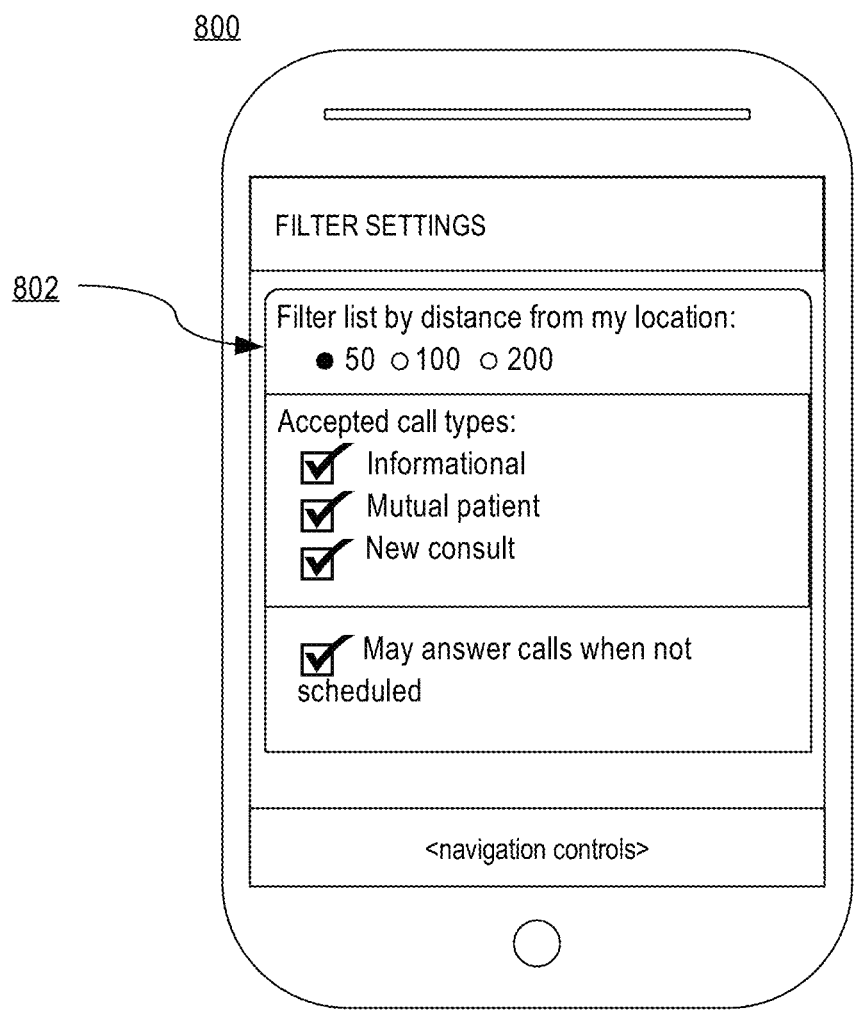
FIG. 8 illustrates an example graphical user interface that is configured to enable a user to specify consultant search filters and other system configuration settings.

FIG. 8 illustrates an example graphical user interface that is configured to enable a user to specify consultant account search filters and other system configuration settings. In an embodiment, GUI 800 comprises a settings panel 802 which includes several interface components enabling a user to specify one or more configuration settings. For example, settings panel 802 may include buttons or other interface elements that enable a user to select a particular distance in which searches for consultant accounts may be confined. By selecting the radio button marked "50," for example, searches for consultant accounts may be confined to an area within 50 miles of the user. The user's location may be determined by the user specifying a location (e.g., the user's office address) or by detecting the location of the user's device using GPS or other location determining technologies.

In some embodiments, the collaboration system may be programmed to store, in data repository 108, data about consultants organized by topic or specialty to assist in finding and ranking individuals who can be identified as top experts in a particular subject based upon objective criteria, to support the process of FIG. 5 and the displays of FIG. 6A, 6B, 6C. For purposes of illustrating an example, suppose that a first consultant is not looking for a list of oncologists, or for a list of breast cancer oncologists, but seeking an expert on BRCA positive, triple-negative breast cancer in the non-European population. Additionally or alternatively, the data repository 108 may organize data about consultants in a hierarchy of specialists, for example cardiologist, preventive cardiologist, cholesterol expert, expert on genetics of cholesterol. To support locating consultants that meet specific criteria of this type, the data repository 108 may store tables or indexes that reflect highly specific areas of expertise. For example, in an embodiment, the collaboration system is programmed to crawl or browse database sources such as textbooks, journal reviews, articles, lectures, patents, citations, social media references, relevant committees and so forth. The data repository 108 may comprise a database table in which rows represent consultants and columns represent attributes of the consultant. A data item identifying a citation to a particular resource such as one of the textbooks, journal reviews, articles, lectures, patents, citations, social media references, relevant committees and so forth may be stored in a column of a consultant record to indicate that the associated consultant is an author or was otherwise identified in the resource. A separate table may store resource records that associate resource identifiers with weight values that specify the quality, importance or relevance, in terms of ranking a consultant, of the associated resource. For example, a peer-reviewed scientific journal may have a higher weight value than a consumer-oriented publication. Ranking consultants may comprise the collaboration system retrieving a consultant record and, for each resource identified in the consultant record, retrieving the weight value for that resource and using the weight values to create a weighted score of the rank of the consultant record.

User search queries may be processed against the data repository 108 to return a result set of consultant records having attribute values for expertise that match keywords in the search queries. The result set may be ranked or ordered based upon the weighted score of each consultant, either as an absolute value or within a particular specialty or field. Ranked search results of this type may be used either to find a consultant for purposes of scheduling a consulting request or call, or after a consulting call to locate reference materials to provide to the other party in the call.

3.4.2 Care Team Scheduling

In an embodiment, a user may desire to establish a consultation with two or more other users at the same time. For example, a physician may be working with two or more other physicians in the treatment of a mutual patient and the physician may desire to consult with each of the other physicians in order to discuss an issue related to the mutual patient. In this context, a group of three or more users may be referred to herein as a "care team," and a consultation involving three or more users may be referred to as a "care team consultation."

Referring again to FIG. 5, in Step 502, input may be received from a user selecting more than one consultant account. For example, FIG. 9 illustrates an example GUI that is configured to enable a user to select two or more other users for a care team consultation.

Figure 9:
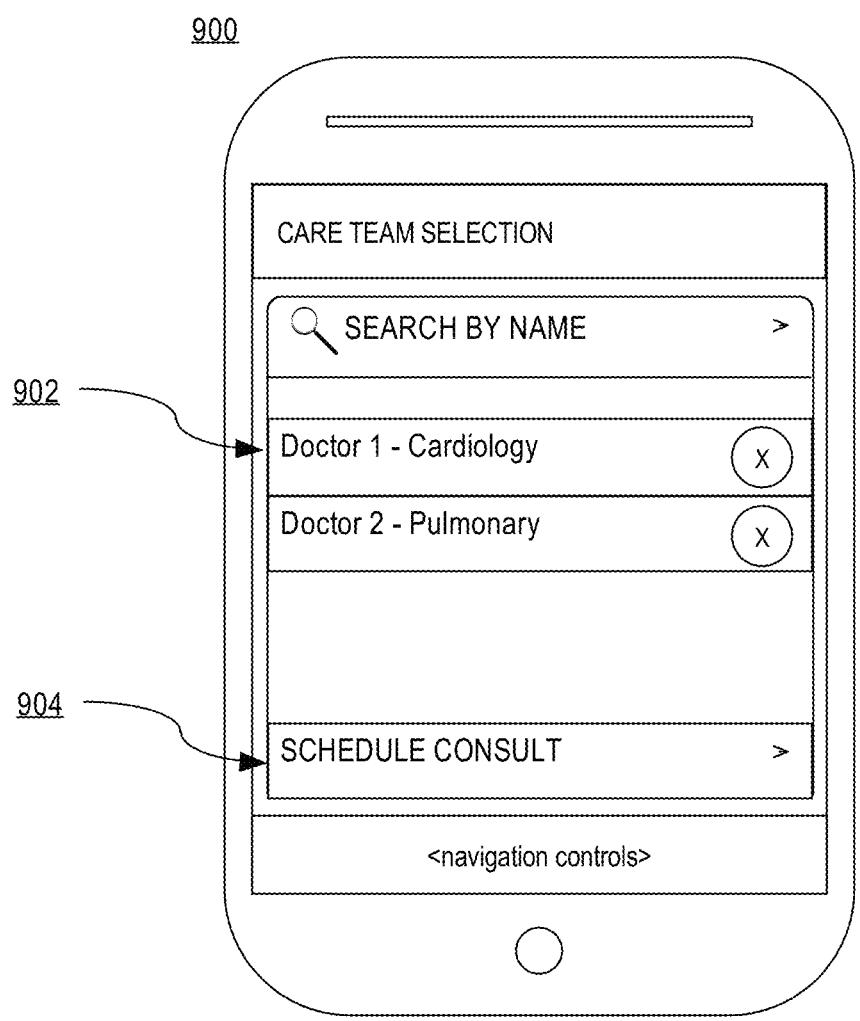
FIG. 9 illustrates an example graphical user interface that is configured to enable a user to select two or more other users for a care team consultation.

In an embodiment, FIG. 9 comprises selected consultant list 902 and care team consultation scheduling button 904. Selected consultant list 902 displays a list of consultant accounts currently selected by a user for participation in a care team consultation. For example, the consultant accounts displayed in consultant list 902 may have been individually selected by a user using the consultant search processes described above, or the consultant accounts may be part of a pre-defined consultant network selected by the user. A consultant list 902 may display information about each consultant account currently in the list and may provide interface mechanisms for removing a consultant account from the list or for adding additional consultant accounts to the list. In an embodiment, a user may proceed with scheduling a care team consultation time with the consultant accounts listed in consultant list 902 by selecting care team consultation scheduling button 904.

Referring again to FIG. 5, in Step 504, it is determined whether the user has selected more than one other consultant account for a consultation. For example, it may be determined that a user has selected more than one consultant account for a care team consultation as illustrated in FIG. 9. In an embodiment, if it is determined that the user has selected more than one other consultant account, the process proceeds to FIG. 10 for the scheduling of a care team consultation.

Figure 10:
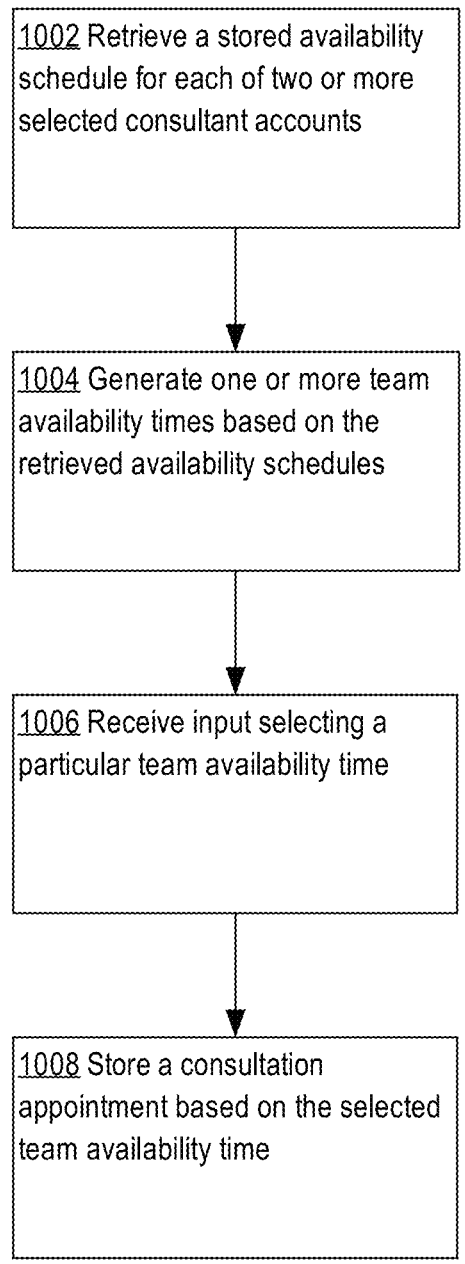
FIG. 10 illustrates a computer-implemented process for scheduling a care team consultation involving three or more users.

FIG. 10 illustrates a process for scheduling a care team consultation involving three or more users. For example, a user may select two or more consultant accounts for a care team consultation, as described above. In Step 1002, a particular availability schedule is retrieved for each of the two or more selected consultant accounts. For example, a stored availability schedule may be retrieved for each of the consultant accounts listed in a selected consultant list as illustrated in FIG. 9.

In Step 1004, one or more team availability times are generated based on the retrieved availability schedules. In general, a team availability time represents an availability period that is present in the availability schedule associated with each of the two or more selected consultant accounts. For example, if a user has selected both a Consultant A and a Consultant B for a care team consultation, if Consultant A has specified an availability period on Thursdays from 5 PM to 6 PM and 6 PM to 7 PM and Consultant B has specified an availability period on Thursdays only from 6 PM to 7 PM, then the period from 6 PM to 7 PM on Thursdays may be selected as a team availability period for a care team consisting of Consultant A and Consultant B.

In Step 1006, input is received selecting a particular team availability period. For example, a user may be presented with a list or other display of all generated team availability times. The user may select a listed availability period to cause scheduling of a care team consultation during the selected availability period. For example, in response to a user selection of a particular availability period, a request may be sent to an application server 106 causing the server to store a consultation appointment based on the particular team availability period.

Figure 11A:
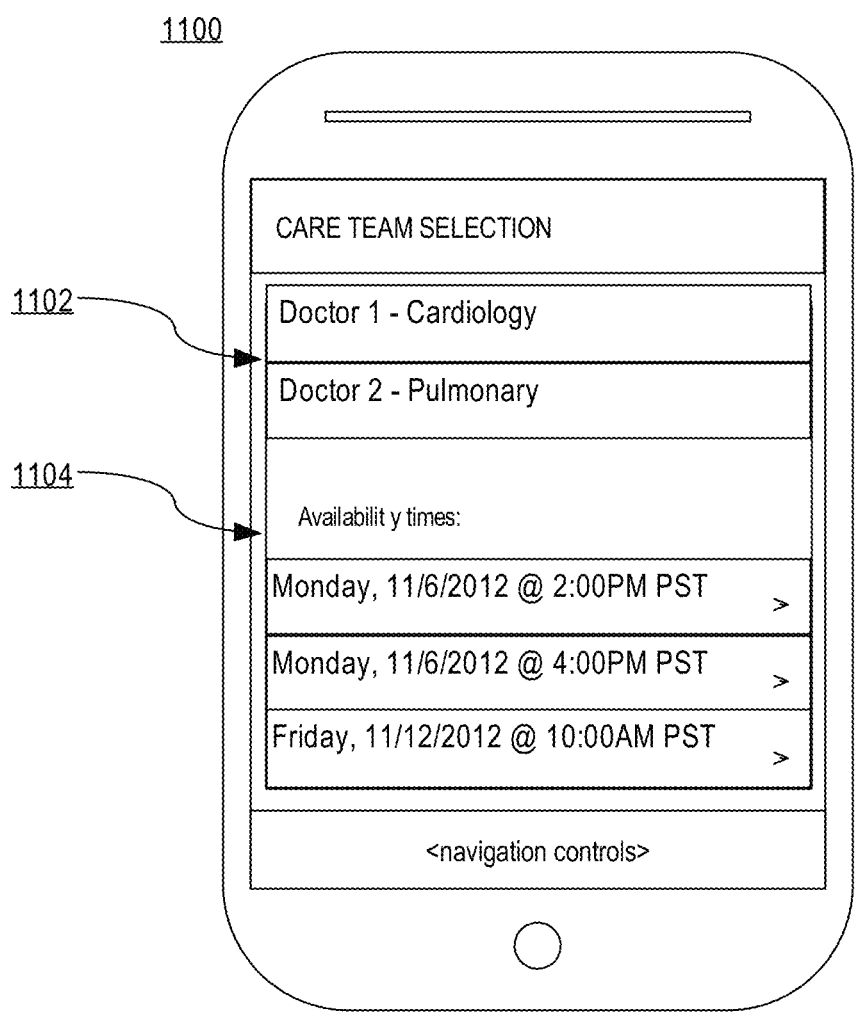
FIG. 11A, FIG. 11B illustrate example graphical user interfaces that are configured to enable a user to schedule a care team consultation.
Figure 11B:
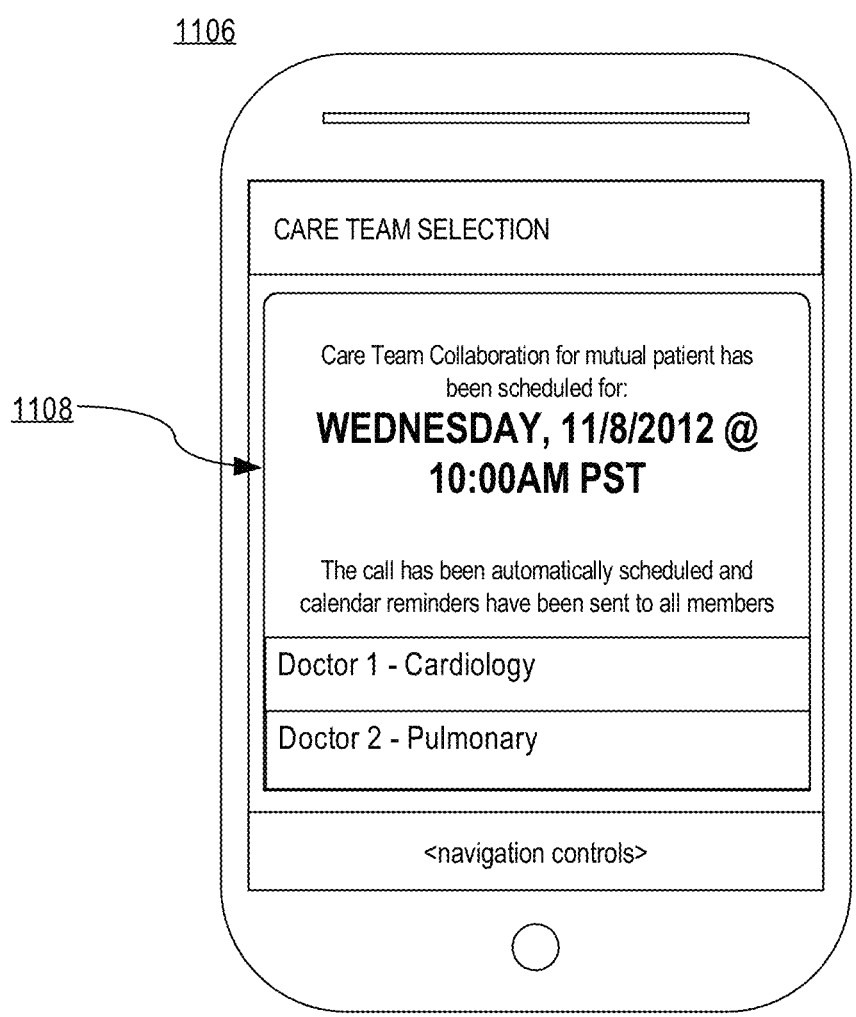

FIG. 11A, 11B illustrate example GUI that are configured to enable a user to schedule a care team consultation. In an embodiment, FIG. 11A comprises a GUI 1100 that includes a care team consultant list 1102 and a care team availability period list 1104. Care team consultant list 1102 displays a list of the consultant accounts that have been selected by a user for participation in the care team consultation. Care team availability period list 1104 comprises a list of generated care team availability periods based on the availability periods of the consultant accounts listed in consultant list 1104. For example, the availability period list depicted in GUI 1100 indicates that each of the users associated with the consultant accounts in list 1102 has indicated an availability period of Monday, November 6 at 2:00 PM PST. In an embodiment, a user may select a care team availability period in the list 1104 in order to confirm scheduling of a consultation at the indicate time.

FIG. 11B illustrates an example GUI 1106 displaying information about a scheduled care team consultation. In an embodiment, GUI 1106 comprises a care team consultation information display that includes information about the care team consultation scheduled by the user including a time for the consultation and a list of the participating consultant accounts.

Referring again to FIG. 10, in Step 1008, a consultation appointment is stored based on the selected team availability time. For example, information about the consultation appointment may be stored in a data repository 108 or in an external calendar service. In an embodiment, an email, calendar alert, or other notification may be sent to each user scheduled to participate in the care team consultation notifying the users of the scheduled time and other participants. In an embodiment, the consultation appointment may cause the server to facilitate a consultation between each of the users during the availability period associated with the consultation appointment.

3.4.3 Establishing a Consultation

In an embodiment, the healthcare collaboration system may facilitate a consultation between two or more users by establishing communications between the users during a specified availability period. An established consultation may allow the users to discuss any questions or issues one user may have for one or more of the other users over an audio, video, or text based communications link. For example, a physician may wish to discuss a particular medical issue that is within another physician's area of expertise and schedule a consultation with the physician during an availability period specified by the physician. By facilitating the consultation at the specified availability period, each of the users may have an opportunity to discuss the matters at a time that is convenient for each user.

Referring again to FIG. 5, in Step 506, input is received indicating selection of an availability period. For example, input selecting an availability period may be received as a result of a user selecting a current availability period as indicated by a consultant account profile or as a result of a user scheduling a consultation for a future availability period. Thus, in various embodiments, a consultation may be initiated directly in response to user input at a client device (e.g., a user selecting a "Call Now" button on a consultant account profile) or based on scheduling information (e.g., a scheduled care team consultation) stored in a data repository 108 or in an external scheduling service.

In Step 508, a consultation is facilitated between the users during the selected availability period. In one embodiment, facilitating a consultation between two or more users may comprise establishing one or more of a phone connection, a voice over Internet Protocol (VoIP) connection, a video conference connection, an online chat, or any other communications link between the two or more users during the specified availability period. For example, an application server 106 may establish communications with each user based on the phone numbers, email addresses, IP addresses, or other information associated with each user's consultant account.

In an embodiment, establishing a communication with a user by an application server 106 may comprise sending to each user a notification message that includes information about the consultation such as the name of the other users and a type of consultation that is being requested (e.g., informational, mutual patient, new patient). In one embodiment, the notification may be presented on a client device 102 as a text alert, an audio alert, or any other type of alert that indicates the information.

In an embodiment, after communications are established with each of the users, the users may conduct the consultation as they desire by communicating over the communications link established with the other users. An application server 106 may monitor and track certain aspects of the consultation including a time elapsed and may record and store audio or other information generated during the consultation. In an embodiment, information about a particular consultation may be stored by an application server 106 as part of a consultation record.

In some embodiments, after a consultation or otherwise in association with the process of searching for a consultant, establishing a consultation call and conducting a consultation, the collaboration system may be programmed to receive a SAVE TO CHART command invocation from a user via the graphical user interface that is described in other sections here. In response, the collaboration system is programmed to save the consultation record as part of a patient chart, electronic medical record, digital data file, or other digital database, repository or storage. In some embodiments, the SAVE TO CHART command may cause the collaboration system to prompt the user to confirm, via responsive input with a computing device, that the user has a relationship of privacy or confidentiality with the subject of the chart, record or file. Examples may include a physician-patient relationship, attorney-client relationship or other relationship that is protected in law or practice. In some embodiments, other steps in the consultation search, initiation, call and completion process may prompt the user to specify whether a confidential, fiduciary or other relationship exists between the user and another subject, and the response to that prompt may determine whether the save operation will execute.

In some embodiments, the process of initiating a consultation may involve contacting a consultant who has not previously participated in the consulting call processes as described herein. For example, assume that a first consultant has used the searching capabilities previously described to identify Jane Smith, who is an expert in BRCA-positive, triple-negative breast cancer in non-European populations, but who has never participated in a consulting call using the system as described herein. In response to selection of Jane Smith as the target of a consulting call, the application server 106 is programmed to dispatch an e-mail message or text message to the consultant with the following content: a request to participate in a consultation call; a brief profile of the sending consultant; and a brief profile of the entity that owns or operates the application server 106 or other elements of the system that is described herein. If an affirmative response is received, then call completion occurs as previously described. In this manner, the searching and call initiation process described above may effectively increase the number of consultants who are available for consultations in the system.

3.4.4 Reference Bookmarking

In an embodiment, in addition to facilitating consultations, the collaboration system may further enable users to add, categorize, and share reference materials with other users in the system. For example, based on issues discussed during a consultation call between two physicians, one of the physicians may desire to share a particular web-accessible medical reference with the other physician. In one embodiment, a user may share a particular reference by using a client device 102 to send a uniform resource locator (URL) and other information about the reference to an application server 106. An application server 106 receiving the information may store the information in association the user's consultant account and, in response to a subsequent request from the user, in association with a particular consultation record. By storing the information in association with a consultation record, others users that participated in the consultation may access the information by viewing a display of the consultation record.

In general, a reference shared by a user may represent information such as guidelines, position papers, original research, review articles, or other information that may be of interest to users participating in consultation. In an embodiment, a shareable reference generally may include any web-accessible resource such as a web page, document file, video file, or audio file accessible by a web browser or other application running on a client device. The reference and resource types identified above are provided only as examples and the types of reference materials that may be stored and shared in the system is not limited to any particular type of reference material or subject matter.

Figure 12:
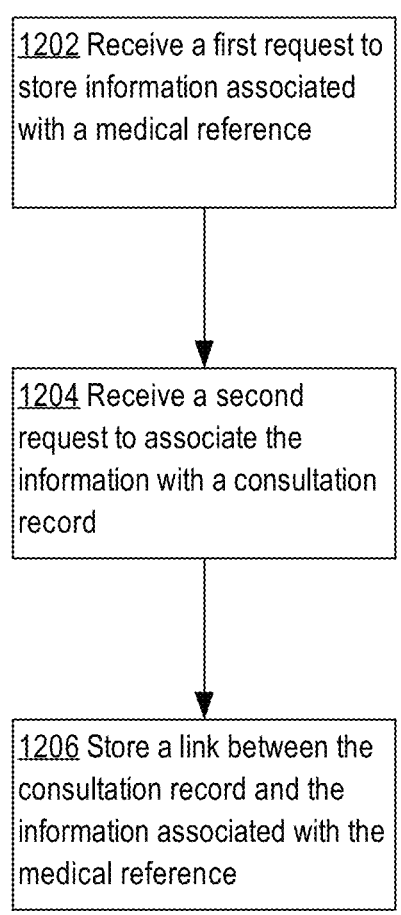
FIG. 12 illustrates a computer-implemented process for receiving and storing information related to a medical reference resource and for associating the information with a consultation record in accordance with an embodiment.

FIG. 12 illustrates a computer-implemented process for receiving and storing links and other information related to web browser accessible medical reference materials and for associating the information with a consultation record. In Step 1202, a first request is received to store information associated with a web browser accessible medical reference. For example, the request may be generated in response to user interaction with a web browser or other application running on a client device 102. In one particular embodiment, the request may be generated by user interaction with a "bookmarklet" configured to execute within a web browser hosted by a client device 102. The medical reference may, for example, be a web page that includes information related to a particular medical specialty or procedure, such as a medical guidelines document.

Figure 13:
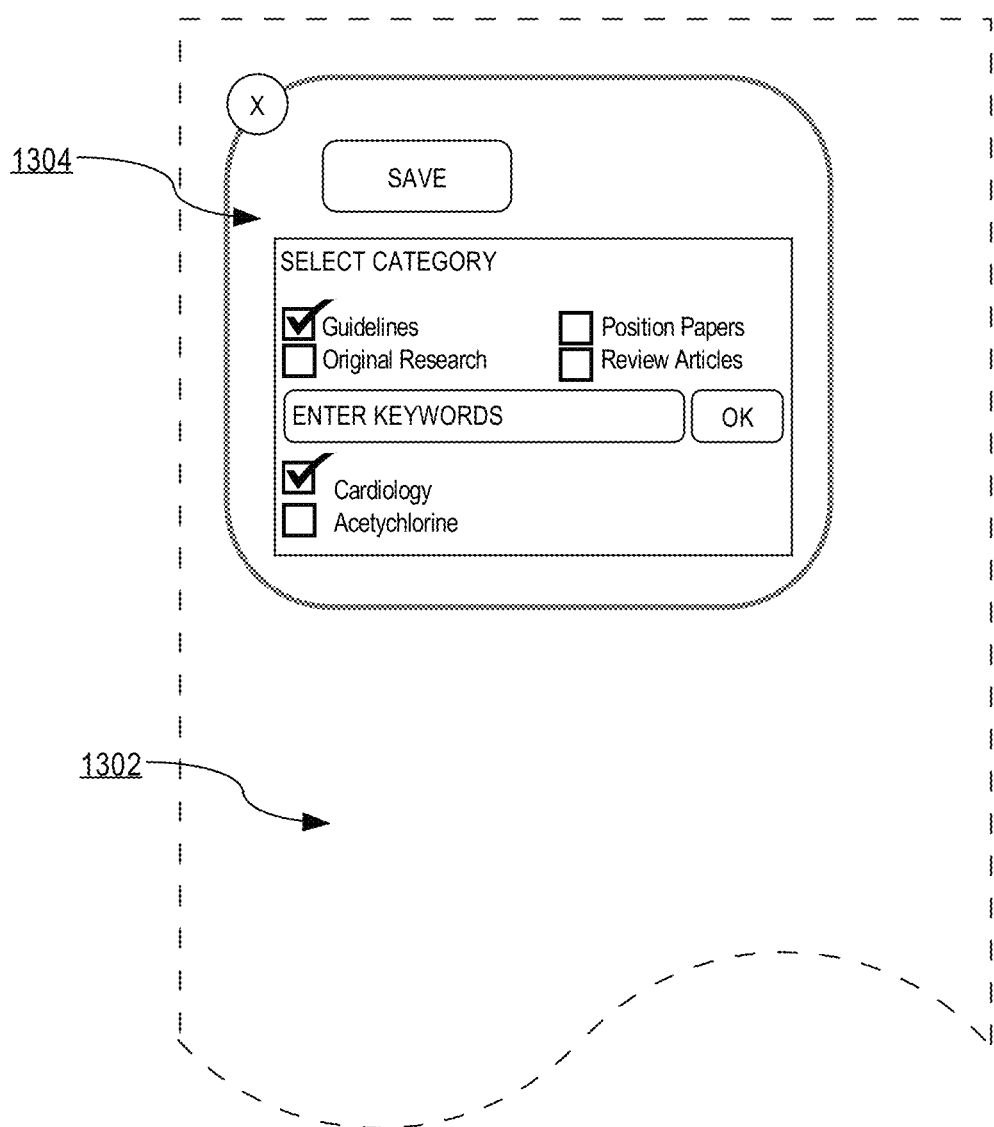
FIG. 13 illustrates an example graphical user interface that is configured to enable a user to add and to categorize a medical reference using a client device.

FIG. 13 illustrates an example GUI that is configured to enable a user to add and categorize a particular medical reference using a client device. In an embodiment, FIG. 13 comprises a resource 1302 and a bookmarklet interface

1304. Resource 1302 may be a web page or other resource accessible by a user using a client device 102. For example, resource 1302 may be a web page that a user has directed a browser running on a client device 102 to display by providing URL for the resource.

In an embodiment, a bookmarklet interface 1304 comprises a graphical display that may be generated by script commands or other logic that run within a web browser. For example, bookmarklet interface 1304 may be generated in response to a user selecting a "bookmark" stored in the web browser and containing commands for generating bookmarklet interface 1304. The bookmarklet interface 1304 may be displayed, for example, as an overlay on the resource 1302 displayed in a web browser.

In an embodiment, bookmarklet interface 1304 may comprise logic that enables user to provide login credentials for authentication with the healthcare consulting system hosted by an application server 106. For example, before display of the particular bookmarklet interface 1304 depicted in FIG. 13, a user may be prompted to provide a username and password that is sent to an application server 106 for authentication. By authenticating a user as a registered user of the system, any information saved by the user using bookmarklet interface 1304 may be stored by application server 106 in association with the user's consultant account.

In an embodiment, a user may provide input to the bookmarklet interface 1304 that categorizes and indicates other information about the resource 1302, including specification of one or more reference categories and/or one or more user-defined keywords or tags. For example, a user may select one or more of the checkboxes displayed in bookmarklet interface 1304 to select particular categories associated with resource 1302. The user may further provide input into the displayed textbox specifying one or more custom keywords or tags, or the user may select one or more keywords or tags from a list of previously specified keywords and tags. In an embodiment, a user may cause information about the resource 1302, including the user provided information, to be saved in association with the user's consultant account by selecting an interface component such as the "Save" button illustrated in bookmarklet interface 1304, thereby causing the information to be sent to an application server 106 for storage. In an embodiment, information related to resource 1302 sent to an application server 106 may include one or more of a URL of the resource, a title associated with the resource, content within the resource, any user-specified categories, keywords, and/or tags.

Referring again to FIG. 12, in Step 1204, a second request is received to associate the information about a medical reference with a consultation record. For example, a first user may desire to share a reference saved by the first user with a second user with whom the first user recently conducted a consultation. In an embodiment, the first user may share the resource with the second user by causing the information about the reference to be associated with a consultation record generated to represent the consultation that occurred between the users. The user may cause the reference to be associated with a particular consultation record, for example, by using one or more interfaces displayed on a client device 102 to view the consultation record and to select the reference the user desires to associate with the consultation.

In Step 1206, based on a request to associate information about a medical reference with a consultation record, a link is stored between the consultation record and the information about the medical reference. For example, in response to receiving a request to associate information about a particular reference with a particular consultation record, an application server 106 may store a link between the reference and the consultation record in a data repository 108.

In one embodiment, an application server 106 may generate an alert in response to storing a link between a reference and a consultation record. For example, an email, text message, or other alert may be sent to any users associated with the consultation record to alert the users that the medical reference has been associated with the consultation record. The users associated with the consultation record may view a shared reference by viewing the consultation record using a client device 102 and selecting the reference associated with the consultation record by another user. For example, user selection of a reference using a client device 102 may cause a web browser or other application running on the client device 102 to open a URL enabling the user to view the medical reference.

While FIG. 12, FIG. 13 have been described in connection with medical references for purposes of illustrating example embodiments, in other embodiments the references may be non-medical. References could be technical references in any suitable field such as engineering, computing, biology, and so forth.

Figure 14A:
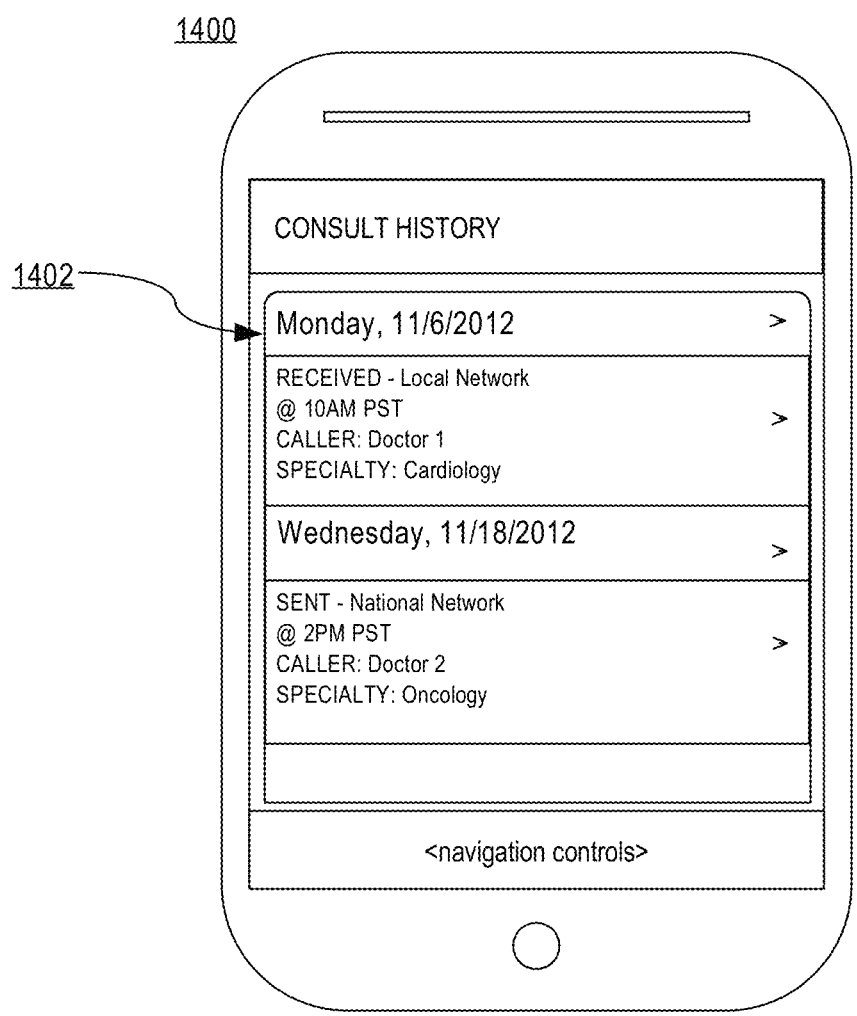
FIG. 14A, 14B illustrate example graphical user interfaces configured to display a user's consultation history and, in response to selection of a particular consultation record from the user's consultation history, to display information associated with the particular consultation record including bookmarked reference materials.
Figure 14B:
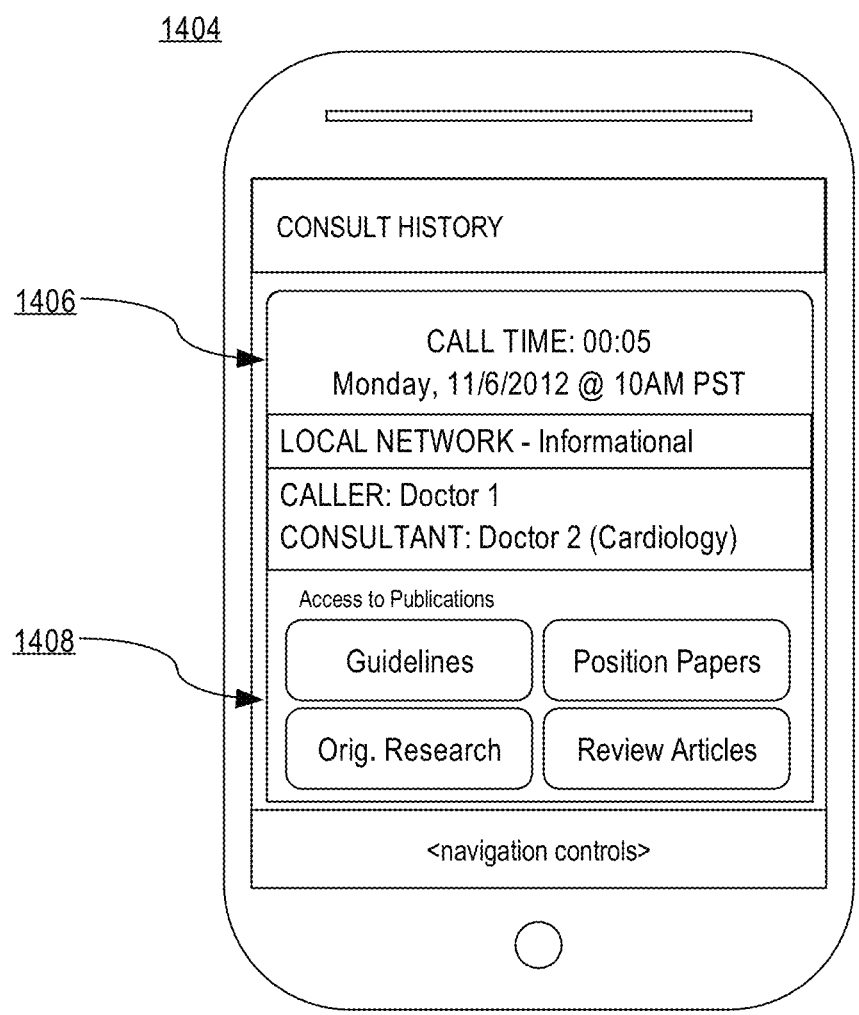

FIG. 14A, 14B illustrate example graphical user interfaces configured to display a user's consultation history and, in response to selection of a particular consultation record from the user's consultation history, to display information associated with the particular consultation record including bookmarked reference materials. For example, FIG. 14A illustrates an example GUI 1400 configured to display a user's consultation history. In an embodiment, GUI 1400 comprises a consultation history list 1402. A consultation history list 1402 comprises information about one or more past consultations that included the user viewing the list. Each consultation record displayed in the list may include information such as the time and date the consultation occurred, whether the consultation was initiated by the user or by another user, and the names and specialties of the other participating users. In an embodiment, a user may select an entry from the consultation history list 1402 in order to view additional information about a particular consultation.

In an embodiment, FIG. 14B illustrates an example GUI 1404 displaying information related to a selected consultation record from a user's consultation history. In an embodiment, GUI 1404 comprises consultation information panel 1406 and reference materials panel 1408. Consultation information panel 1406, for example, may display information about the particular consultation such as the time and date of the call, a duration of the call, a consultant network associated with the consultation participants, a consultation type, and the names of the participating consultants.

In an embodiment, reference materials panel 1408 comprises one or more buttons that may be configured to provide access to reference materials associated with the consultation record by other users or to enable a user to attach new reference materials. For example, a user may select the "Guidelines" button in reference materials panel 1408 to view any reference materials attached by other users and categorized as a "Guidelines" reference material. In an embodiment, the display of the buttons in reference materials panel 1408 may change depending on whether there are any attached documents of the type indicated by the button. For example, the "Position Papers" button may be shaded green or include a number if there are any attached reference materials categorized as a "position paper," while the "Review Articles" button may be shaded red if there are no attached reference materials of that category.

Figure 15:
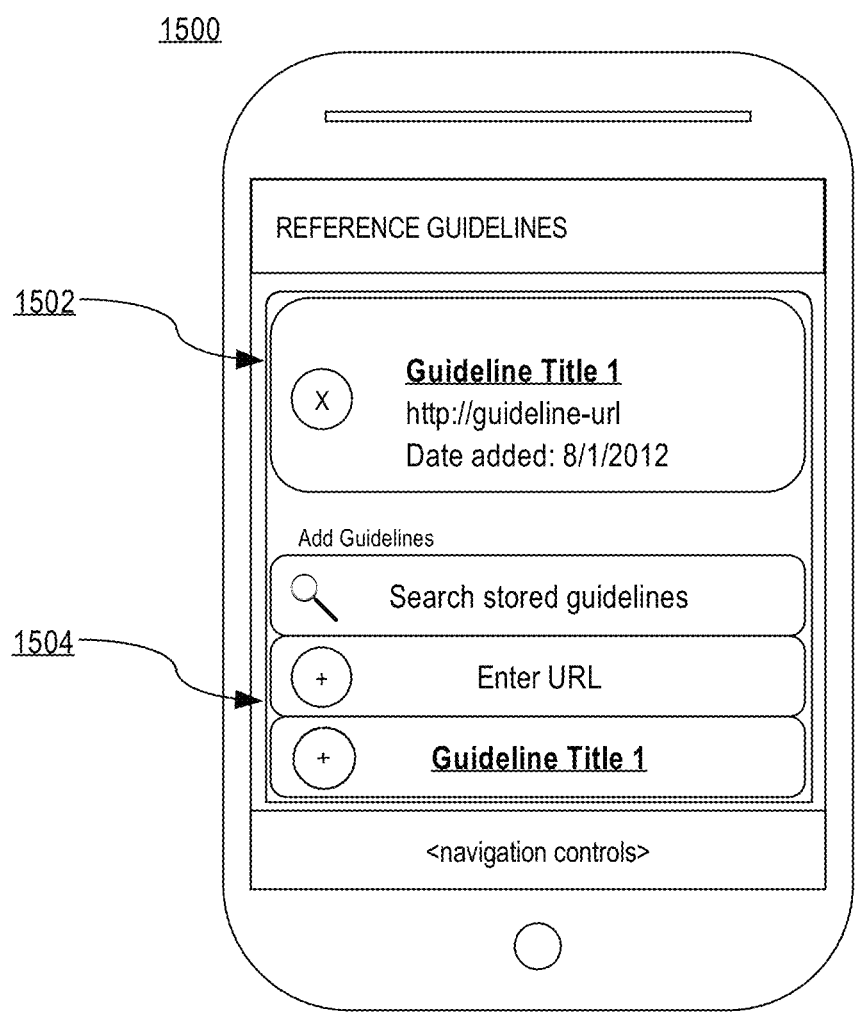
FIG. 15 illustrates an example graphical user interface configured to enable a user to associate one or more saved medical reference materials with a consultation record.

In an embodiment, a user may use one or more interface displays to associate one or more reference material saved by the user with a consultation record. FIG. 15 illustrates an example GUI 1500 configured to enable a user to associated one or more saved referenced materials with a consultation record. In an embodiment, FIG. 15 comprises attached reference materials 1502 and reference attachment buttons 1504. Attached reference materials 1502 may display one or more reference materials that have been previously attached to a consultation record.

Reference attachment buttons 1504 illustrate example interface components that enable a user to add one or more saved referenced materials to a consultation record. For example, reference attachment buttons 1504 may include an interface component that enables a user to search for a reference material by name or by selecting a saved reference material link from a list. In an embodiment, after a user has associated one or more reference material links with a consultation record, the reference material links may be viewed by other users associated with the consultation record by using a display similar to the display illustrated in FIG. 14B.

3.5 Post-Consultation

In various embodiments, the healthcare consulting system may be configured to enable users to perform various operations related to consultations in which a user has participated. For example, the system may be configured to enable users to provide survey information related to consultations in which a user participated, to rate reference materials associated with a consultation record by other users, and to receive compensation for time spent conducting consultations requested by other users.

In one embodiment, after a consultation has ended, one or more of the users participating in the consultation may be prompted to complete a survey related to the consultation. For example, the survey may be displayed on a client device 102 in response to a user closing the communications link for the consultation. The survey may enable a user to provide a rating for various aspects of the consultation including the helpfulness, quality, knowledge, and other factors related to the user's interaction with the other users during the consultation. In an embodiment, a user may submit the survey results to an application server 106 and the provided survey ratings may be stored in association with the consultation record and/or the other user's consultant account records.

In another embodiment, users may be able to view and rate reference materials shared by others. A user may view the reference materials shared by others by viewing the references as attachments to consultation records, as described above. A user may rate an attached reference material by providing a rating value or other input such as "liking" the reference material using one or more provided interface mechanisms. The user ratings may be stored in association with the reference material information and used to generate various statistics about the perceived value of particular reference materials to the user community.

In one embodiment, the system may be configured to compensate users for time spent participating in consultations. For example, if a first user initiates a consultation with a second user, the second user may be compensated for the time the second user spends consulting with the first user. In one embodiment, an application server 106 may be configured to track and record an amount of time that each user spends conducting consultations initiated by other users. Based on the amount of time recorded, the system may automate payments to users on a monthly or other periodic basis for their time. The payment amount for a particular user may based on a set rate and/or based on any number of factors including, for example, survey results for consultations in which the user participated, a number of reference materials shared by the user, and user ratings of reference materials shared by the user.

In another embodiment, upon completion of a consulting call, the application server 106 is programmed to cause displaying a graphical user interface widget or an interface panel that prompts the user to select a type of consulting call that just occurred. In one embodiment, type values for completed calls include Informational, Mutual or New Consult. In response to selection of a particular type value, the application server 106 processes records of the completed call in different ways.

In one embodiment, in response to a type value of Informational, the application server 106 is programmed not to store or save any information about the call, including a call record; optionally, reference material still can be forwarded to the other party using the reference material processes that have been described herein.

In an embodiment, in response to a type value of Mutual, the application server 106 is programmed to store a consultation call record at another computer system. As examples, the other computer system may host an electronic medical record (EMR) system with individual patient charts, or the other computer system may host a billing system. In an embodiment, with a type value of Mutual, the application server 106 calls an API of the other computer system and provides a copy of a consulting call record to store in the other computer system using programmatic mechanisms of the other computer system that are accessed via the API. In some embodiments, storing the consultation call record may include storing a value for the duration of the call; storing a text transcript of the call, which may include requesting an external service to create a transcript based on an audio file and receiving the transcript in a response from the external service; or storing reference material as part of the consultation call record, where the reference material may be text, images, video, hyperlinks or URLs.

In an embodiment, with a type value of New Consult, the application server 106 is programmed to process the call in the same manner described above for a type value of Mutual, except that a record specifying the occurrence of a new consultation request also is stored in the other computer system, with a timestamp.

4.0 Example Implementation Mechanism—Hardware Overview

Figure 16:
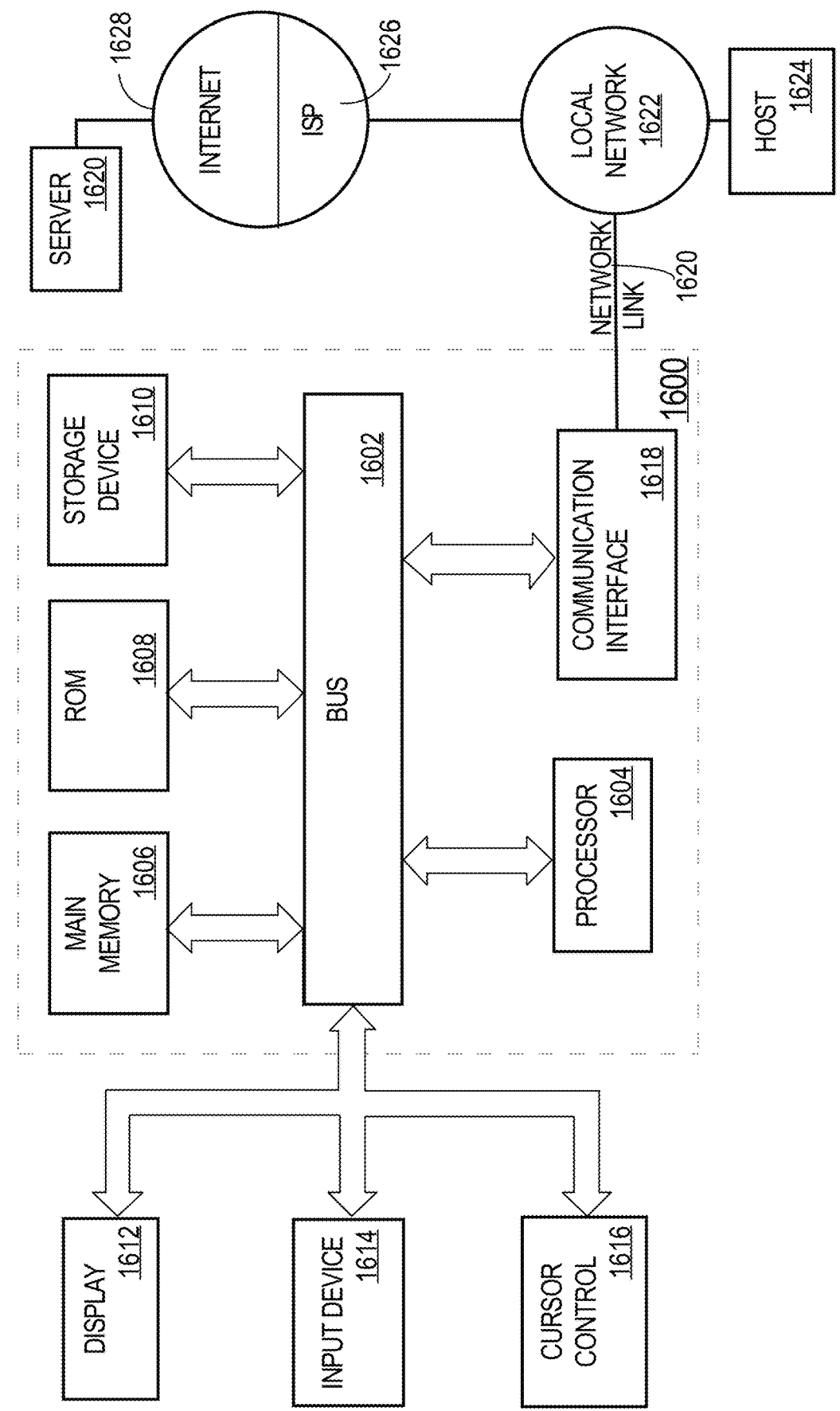
FIG. 16 illustrates an example of a computer upon which one or more embodiments may be implemented.

FIG. 16 is a block diagram that illustrates a computer system 1600 upon which an embodiment may be implemented. Computer system 1600 includes a bus 1602 or other communication mechanism for communicating information, and a processor 1604 coupled with bus 1602 for processing information. Computer system 1600 also includes a main memory 1606, such as a random access memory (RAM) or other dynamic storage device, coupled to bus 1602 for storing information and instructions to be executed by processor 1604. Main memory 1606 also may be used for storing temporary variables or other intermediate information during execution of instructions to be executed by processor 1604. Computer system 1600 further includes a read only memory (ROM) 1608 or other static storage device coupled to bus 1602 for storing static information and instructions for processor 1604. A storage device 1610, such as a magnetic disk or optical disk, is provided and coupled to bus 1602 for storing information and instructions.

Computer system 1600 may be coupled via bus 1602 to a display 1612, such as a liquid crystal display (LCD), for displaying information to a computer user. In other embodiments, a display 1612 may represent LED indicator lights and other electronic displays. An input device 1614, including alphanumeric and other keys, touchscreen sensors, and device buttons, is coupled to bus 1602 for communicating information and command selections to processor 1604.

The invention is related to the use of computer system 1600 for implementing the techniques described herein. According to one embodiment, those techniques are performed by computer system 1600 in response to processor 1604 executing one or more sequences of one or more instructions contained in main memory 1606. Such instructions may be read into main memory 1606 from another machine-readable medium, such as storage device 1610. Execution of the sequences of instructions contained in main memory 1606 causes processor 1604 to perform the process steps described herein. In alternative embodiments, hard-wired circuitry may be used in place of or in combination with software instructions to implement the invention. Thus, embodiments are not limited to any specific combination of hardware circuitry and software.

The term "machine-readable medium" as used herein refers to any medium that participates in providing data that causes a machine to operation in a specific fashion. In an embodiment implemented using computer system 1600, various machine-readable media are involved, for example, in providing instructions to processor 1604 for execution. Such a medium may take many forms, including but not limited to storage media and transmission media. Storage media includes both non-volatile media and volatile media. Non-volatile media includes, for example, optical or magnetic disks, such as storage device 1610. Volatile media includes dynamic memory, such as main memory 1606. Transmission media includes coaxial cables, copper wire and fiber optics, including the wires that comprise bus 1602. Transmission media can also take the form of acoustic or light waves, such as those generated during radio-wave and infra-red data communications. All such media must be tangible to enable the instructions carried by the media to be detected by a physical mechanism that reads the instructions into a machine.

Common forms of machine-readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, and EPROM, a FLASH-EPROM, any other memory chip or cartridge, a carrier wave as described hereinafter, or any other medium from which a computer can read.

Various forms of machine-readable media may be involved in carrying one or more sequences of one or more instructions to processor 1604 for execution. For example, the instructions may initially be carried on a magnetic disk of a remote computer. The remote computer can load the instructions into its dynamic memory and send the instructions over a telephone line using a modem. A modem local to computer system 1600 can receive the data on the telephone line and use an infra-red transmitter to convert the data to an infra-red signal. An infra-red detector can receive the data carried in the infra-red signal and appropriate circuitry can place the data on bus 1602. Bus 1602 carries the data to main memory 1606, from which processor 1604 retrieves and executes the instructions. The instructions received by main memory 1606 may optionally be stored on storage device 1610 either before or after execution by processor 1604.

Computer system 1600 also includes a communication interface 1618 coupled to bus 1602. Communication interface 1618 provides a two-way data communication coupling to a network link 1620 that is connected to a local network 1622. For example, communication interface 1618 may be an integrated services digital network (ISDN) card or a modem to provide a data communication connection to a corresponding type of telephone line. As another example, communication interface 1618 may be a local area network (LAN) card to provide a data communication connection to a compatible LAN. Wireless links may also be implemented. In any such implementation, communication interface 1618 sends and receives electrical, electromagnetic or optical signals that carry digital data streams representing various types of information.

Network link 1620 typically provides data communication through one or more networks to other data devices. For example, network link 1620 may provide a connection through local network 1622 to a host computer 1624 or to data equipment operated by an Internet Service Provider (ISP) 1626. ISP 1626 in turn provides data communication services through the world wide packet data communication network now commonly referred to as the "Internet" 1628. Local network 1622 and Internet 1628 both use electrical, electromagnetic or optical signals that carry digital data streams. The signals through the various networks and the signals on network link 1620 and through communication interface 1618, which carry the digital data to and from computer system 1600, are exemplary forms of carrier waves transporting the information.

Computer system 1600 can send messages and receive data, including program code, through the network(s), network link 1620 and communication interface 1618. In the Internet example, a server 1630 might transmit a requested code for an application program through Internet 1628, ISP 1626, local network 1622 and communication interface 1618.

The received code may be executed by processor 1604 as it is received, and/or stored in storage device 1610, or other non-volatile storage for later execution. In this manner, computer system 1600 may obtain application code in the form of a carrier wave.

In the foregoing specification, embodiments have been described with reference to numerous specific details that may vary from implementation to implementation. Thus, the sole and exclusive indicator of what is the invention, and is intended by the applicants to be the invention, is the set of claims that issue from this application, in the specific form in which such claims issue, including any subsequent correction. Any definitions expressly set forth herein for terms contained in such claims shall govern the meaning of such terms as used in the claims. Hence, no limitation, element, property, feature, advantage or attribute that is not expressly recited in a claim should limit the scope of such claim in any way. The specification and drawings are, accordingly, to be regarded in an illustrative rather than a restrictive sense.

What is claimed is:

1. A computer system, comprising:
   an application server computer with scheduling logic that is programmed to cause the application server computer to execute receiving and storing in a data storage device, which is coupled to the application server computer, from a first client device that is associated with a first user and via graphical user interface (GUI)

logic programmed in the first client device, digital data input specifying one or more second users, wherein each of the one or more second users is associated with a particular availability schedule that has been stored in the data storage device, and wherein each of the particular availability schedules specifies two or more particular availability periods;

client device application logic programmed in each of the first client device and a second client device and programmed to cause the second client device to provide the particular availability schedules and two or more particular availability periods to the application server computer over the data network via selection using the GUI logic of two or more days of a week and the two or particular availability periods for selected days of the week using GUI buttons and navigation controls and toggling the two or particular availability periods;

the application server computer further programmed with repository access logic that is programmed to cause the application server computer to perform retrieving from the data storage device, for each second user of the one or more second users, the particular availability schedule associated with said each second user;

the application server computer further programmed with communications logic that is programmed to cause the application server computer to perform receiving, from the first client device, a request to initiate a consultation with said each second user;

wherein the communications logic is programmed to cause the application server computer to perform facilitating a consultation between the first user and said each second user by initiating a phone call between the first client device and second client device, using one or more of a phone connection or a voice over internet protocol (VoIP) connection and by sending to the first user and said each second user a notification message for display on the first client device and the second client device;

wherein the client device application logic is programmed in each of the first client device and the second client device to cause displaying the notification message.

2. The computer system of claim 1, the digital data input also specifying a consultation call type, wherein the scheduling logic is programmed to cause storing the two or more particular availability periods in association with two or more respective different consultation types of a set of consultation types, the consultation type indicating whether particular information can be shared during the one or more particular availability periods, the particular availability schedule associated with said each second user retrieved using the consultation type stored in association with the two or more particular availability periods specified by the particular availability schedule associated with said each second user;

the notification message including a particular type of consultation that is being requested from among the set of consultation types;

wherein the repository access logic is programmed to cause the application server computer to perform creating and storing in the data storage device a consult history record for the phone call upon completion of the phone call and that specifies a particular consultation type from among the set of consultation types that was used for the phone call.

3. The computer system of claim 1, the application server computer further programmed with communications logic that is programmed to cause the application server computer to perform receiving, from the first client device, the request to initiate a consultation with said each second user via the GUI logic using a consultation call button that is displayed graphically using the GUI logic.

4. The computer system of claim 1, wherein the scheduling logic is programmed to cause the application server computer to perform generating, based on the retrieved particular availability schedules, one or more team availability periods, wherein each team availability period of the one or more team availability periods indicates a particular availability period that is present in the particular availability schedule of said each second user and that is stored in association with the consultation type specified by the input;

wherein the scheduling logic is programmed to cause the application server computer to perform receiving input selecting a particular team availability period of the one or more team availability periods;

wherein the repository access logic is programmed to cause the application server computer to perform storing, in the data storage device, a consultation appointment based on the particular team availability period.

5. The computer system of claim 4, wherein the communications logic is programmed to cause the application server computer to perform facilitating a consultation during the particular team availability period by initiating, for each of the one or more healthcare consultants and the first client device and second client device, one or more of a video conference, an email conversation, an online chat conversation.

6. The computer system of claim 4, wherein each availability period indicates a time period during which the first user is available to participate in a consultation with other consultants for the specified consultation type.

7. The computer system of claim 4, wherein the scheduling logic is programmed to cause the application server computer to perform, when the availability schedule of the first user does not include the availability period corresponding to the specified time or if the specified one or more particular consultation types specified by the request does not match the one or more consultation types associated with the availability period corresponding to the specified time of the availability schedule of the first user, the availability status of the first user is changed to unavailable for the specified time.

8. The computer system of claim 4, wherein the scheduling logic is programmed to cause the application server computer to perform, when the availability schedule of the first user includes the availability period corresponding to the specified time and if the specified one or more particular consultation types specified by the request matches the one or more consultation types associated with the availability period corresponding to the specified time of the availability schedule of the first user, the availability status of the first user is changed to available for the specified time.

9. The computer system of claim 1, further comprising sending a text alert to the second client device indicating the consultation appointment.

10. The computer system of claim 1, wherein the scheduling logic is programmed to cause the application server computer to perform:

receiving, from the first client device, a first request to store information associated with a web-accessible technical reference;

receiving, from the first client device, a second request to associate the information with the consult history record;

in response to receiving the second request, storing, in the data storage device, a link between the consult history record and the information associated with the technical reference;

generating an alert in response to storing the link between the consult history record and the information associated with the technical reference;

identifying the second client device from the consultation record;

sending the alert to the second client device via email or text message.

11. The computer system of claim 10, wherein the information comprises one or more of a uniform resource locator (URL), a portion of a web page, an image file, a video file, an audio file.

12. The computer system of claim 10, wherein the information comprises one or more of a user-specified reference category and a user-specified tag.

\* \* \* \* \*